US011446271B2

(12) United States Patent
Ludlow et al.

(10) Patent No.: US 11,446,271 B2
(45) Date of Patent: Sep. 20, 2022

(54) METHODS AND COMPOSITIONS FOR INCREASING THE POTENCY OF ANTIFUNGAL AGENTS

(71) Applicant: Pacific Northwest Research Institute, Seattle, WA (US)

(72) Inventors: Catherine Ludlow, Seattle, WA (US); Aimee Dudley, Seattle, WA (US); Zhihao Tan, Singapore (SG)

(73) Assignee: PACIFIC NORTHWEST RESEARCH INSTITUTE, Seattle, WA (US)

( * ) Notice: Subject to any disclaimer, the term of this patent is extended or adjusted under 35 U.S.C. 154(b) by 20 days.

(21) Appl. No.: 16/927,816

(22) Filed: Jul. 13, 2020

(65) Prior Publication Data

US 2020/0338036 A1 Oct. 29, 2020

Related U.S. Application Data

(62) Division of application No. 15/516,879, filed as application No. PCT/US2015/054304 on Oct. 6, 2015, now Pat. No. 10,751,317.

(60) Provisional application No. 62/190,660, filed on Jul. 9, 2015, provisional application No. 62/061,579, filed on Oct. 8, 2014.

(51) Int. Cl.
| | | |
|---|---|---|
| A61K 31/277 | (2006.01) |
| A61K 31/045 | (2006.01) |
| A61K 31/05 | (2006.01) |
| A61K 31/136 | (2006.01) |
| A61K 31/137 | (2006.01) |
| A61K 31/138 | (2006.01) |
| A61K 31/365 | (2006.01) |
| A61K 31/4164 | (2006.01) |
| A61K 31/4196 | (2006.01) |
| A61K 31/496 | (2006.01) |
| A61K 31/505 | (2006.01) |
| A61K 45/06 | (2006.01) |
| A61L 15/44 | (2006.01) |
| A61L 27/34 | (2006.01) |
| A61K 31/506 | (2006.01) |
| A61K 31/704 | (2006.01) |
| A61K 31/5375 | (2006.01) |
| A61L 31/10 | (2006.01) |
| A61K 31/7048 | (2006.01) |
| A61K 31/513 | (2006.01) |
| C12Q 1/18 | (2006.01) |
| A61L 31/16 | (2006.01) |
| A61L 27/54 | (2006.01) |
| A61L 29/08 | (2006.01) |
| A61L 29/16 | (2006.01) |
| A01N 31/04 | (2006.01) |
| A61F 6/04 | (2006.01) |

(52) U.S. Cl.
CPC .......... *A61K 31/277* (2013.01); *A01N 31/04* (2013.01); *A61K 31/045* (2013.01); *A61K 31/05* (2013.01); *A61K 31/136* (2013.01); *A61K 31/137* (2013.01); *A61K 31/138* (2013.01); *A61K 31/365* (2013.01); *A61K 31/4164* (2013.01); *A61K 31/4196* (2013.01); *A61K 31/496* (2013.01); *A61K 31/505* (2013.01); *A61K 31/506* (2013.01); *A61K 31/513* (2013.01); *A61K 31/5375* (2013.01); *A61K 31/704* (2013.01); *A61K 31/7048* (2013.01); *A61K 45/06* (2013.01); *A61L 15/44* (2013.01); *A61L 27/34* (2013.01); *A61L 27/54* (2013.01); *A61L 29/085* (2013.01); *A61L 29/16* (2013.01); *A61L 31/10* (2013.01); *A61L 31/16* (2013.01); *C12Q 1/18* (2013.01); *A61F 6/04* (2013.01); *A61L 2300/404* (2013.01); *G01N 2333/37* (2013.01); *G01N 2333/40* (2013.01)

(58) Field of Classification Search
CPC .............. A61K 31/277; A61K 31/4196; A61K 31/137; A61K 31/496; A61K 31/506; A61K 31/704; A61K 31/5375; A61K 45/06; A61K 31/7048; A61K 31/365; A61K 31/513; A61K 31/4164; A61K 31/045; A61K 31/136; A61K 31/138; A61K 31/505; A61K 31/05; A61L 31/10; A61L 31/16; A61L 27/54; A61L 29/085; A61L 15/44; A61L 29/16; A61L 27/34; C12Q 1/18; A01N 31/04; A61F 6/04; G01N 2333/37
USPC ........................................................... 514/34
See application file for complete search history.

(56) References Cited

U.S. PATENT DOCUMENTS 3,899,578 A 8/1975 Bird et al.
4,995,997 A * 2/1991 Noda .................... C10M 133/12
508/262

(Continued)

FOREIGN PATENT DOCUMENTS

EP 2684456 1/2014
JP 2005 035931 2/2005

(Continued)

OTHER PUBLICATIONS

Corrales et al. Synthesis and Antileishmanial Activity of Lipophilic Aromatic Aminoalcohols. TheScientificWorldJournal (2010) 10, 1067-1072. (Year: 2010).*

(Continued)

*Primary Examiner* — Yih-Horng Shiao
(74) *Attorney, Agent, or Firm* — Knobbe, Martens, Olson & Bear LLP

(57) ABSTRACT

Embodiments provided herein include methods, compositions, and uses of aromatic alcohols to increase the potency of antifungal agents.

22 Claims, 14 Drawing Sheets

(56) References Cited

U.S. PATENT DOCUMENTS

| | | | |
|---|---|---|---|
| 10,751,317 | B2 | 8/2020 | Ludlow et al. |
| 2004/0209852 | A1 | 10/2004 | Chaudry |
| 2007/0004686 | A1 | 1/2007 | Bengtsson et al. |
| 2008/0214568 | A1 | 9/2008 | Remmal |
| 2012/0269740 | A1* | 10/2012 | Rozot .................. A61K 8/41 424/59 |
| 2013/0123205 | A1 | 5/2013 | Tunac |
| 2013/0230609 | A1 | 9/2013 | Modak et al. |
| 2013/0345051 | A1 | 12/2013 | Martinez et al. |
| 2014/0287072 | A1 | 9/2014 | Modak et al. |
| 2017/0296502 | A1 | 10/2017 | Ludlow et al. |

FOREIGN PATENT DOCUMENTS

| | | |
|---|---|---|
| WO | WO 2004/091576 A1 | 10/2004 |
| WO | WO 2011/002929 A1 | 1/2011 |
| WO | WO 2011/121604 A2 | 10/2011 |
| WO | WO 2011/121604 A3 | 3/2012 |
| WO | WO 2011/121604 A9 | 4/2012 |
| WO | WO 2016/057563 A1 | 4/2016 |

OTHER PUBLICATIONS

Albuquerque et al., Quorum Sensing in Fungi—A Review, Medical Mycology Case Reports, vol. 50, No. 4, pp. 337-345, 2012.

Alexander et al., Increasing Echinocandin Resistance in Candida Glabrata: Clinical Failure Correlates With Presence of FKS Mutations and Elevated Minimum Inhibitory Concentrations, Clinical Infectious Diseases, vol. 56, No. 12, pp. 1724-1732, 2013.

Babu et al., Synthesis, Antifungal Activity, and Structure Activity Relationships of Coruscanone A Analogs, Journal of Medicinal Chemistry, vol. 49, No. 26, pp. 7877-7886, 2006.

Bartley et al., The Effect of Metabolic Inhibitors on the Development of Respiration in Anaerobically Grown Yeast, Biochemical Journal, vol. 99, pp. 599-603, 1966.

Benjamin et al., Neonatal Candidiasis Among Extremely Low Birth Weight Infants: Risk Factors, Mortality Rates, and Neurodevelopmental Outcomes at 18 to 22 Months, Pediatrics, vol. 117, Issue1, pp. 84-92, 2006.

Carrillo-Munoz et al., Combination Antifungal Therapy: A Stategy For The Management of Invasive Fungal Infections, Archive of Revista Española de Quimioterapia, vol. 27, No. 3, pp. 141-158, 2014.

Cremer et al., 2,4 (Hydroxyphenly)-Ethanol, An Antioxidative Agent Produced by Candida Spp., Impairs Neutorphillic Yeast Killing In Vitro, FEMS Microbiology Letters, vol. 170 pp. 319-325, 1999.

De Vita et al., Synthesis and Antifungal Activity of a New Series of 2-(1H-Imidazol-1-Yl)-1-Phenylethanol Derivatives, European Journal of Medicinal Chemistry, vol. 49, pp. 334-342, 2012.

Extended European Search Report, dated Sep. 7, 2018, in European Application No. EP 15849315.5.

Falagas et al., Effectiveness and Nephrotoxicity of Intravenous Colistin for Treatment of Patients With Infections Due to Polymyxin-Only-Susceptible (POS) gram-negative bacteria, European Journal of Clinical Microbiology and Infectious Diseases, vol. 25, Issue 9, pp. 596-599, 2006.

Fontenelle et al. Alkylphenol Activity against Candida spp. and Microsporum canis: A Focus on the Antifungal Activity ofThymol, Eugenol and O-Methyl Derivativesm Molecules, vol. 16, pp. 6422-6431, 2011.

Hua et al., The Major Volatile Compound 2-Phenylethanol From the Biocontrol Yeast, Pichia anomala, Inhibits Growth and Expression of Aflatoxin Biosynthetic Genes of Aspergillus Flavus, Mycotoxin Research, vol. 30, Issue 2, 71-78, 2014.

Hube et al., Disruption or Each of the Secreted Aspartyl Proteinase Genes SAP1, SAP2, and SAP3 or Candida albicans Attenuates Virulence, Infection and Immunity, Infection and Immunity, vol. 65, No. 9, pp. 3529-3538, 1997.

International Preliminary Report on Patenability date Apr. 11, 2017 in International application No. PCT/US2015/054304.

International Search Report and Written Opinion dated Dec. 30, 2015 in the international application PCT/US2015/54304.

Jones et al. Oral Dosing (Gavage) in Adult Mice and Rats SOP. UBC Animal Care Guidelines SOP: ACC-2012-Tech09. Date approved: Oct. 2012.

Kosalec et al., Antifungal Activity of 2-Phenylethanol and Levomenthol Against Molds From Indoor Air and Damp Dwellings, Biochemistry Planta Medica, vol. 73, pp. 118, 2007.

Magnusson et al., Lactobacillus coryniformis Subsp. coryniformis Strain Si3 Produces a Broad-Spectrum Proteinaceous Antifungal Compound, Applied and Environmental Microbiology, vol. 67, No. 1, pp. 1-5, 2001.

Martins et al., Effect of Exogenous Administration of Candida Albicans Autoregulatory Alcohols in a Murine Model of Hematogenously Disseminated Candidiasis, Journal of Basic Microbiology, vol. 52, No. 4, pp. 487-491, 2012.

Notification of Defects, dated Jun. 8, 2020, in U.S. Pat. No. 251,588.

Office Action dated Mar. 4, 2020 in European application No. 15 849 315.5.

Ostrosky-Zeichner et al., An Insight Into the Antifungal Pipeline: Selected New Molecules and Beyond, Nature Reviews Drug Discovery, vol. 9, pp. 719-727, 2010.

Partial Search Report dated Apr. 24, 2018 in the European patent application No. 15849315.5.

Pierce et al. Candidiasis Drug Discovery and Development: New Approaches Targeting Virulence for Discovering and Identifying New Drugs, Expert Opinion on Drug Discovery, vol. 8, No. 9, pp. 1117-1126, 2013.

Politeo et al. Chemical Composition and Antioxidant Capacity of Free Volatile Aglycones From Basil (Ocimum basilicum L.) Compared With Its Essential Oil, Food Chemistry 101, pp. 379-385, 2007.

Scheller et al. Synergism Between Ethanolic Extract of Propolis (EEP) and Anti-Tuberculosis Drugs on Growth of Mycobacteria, Zeitschrift Für Naturforschung C, vol. 54, No. 7-8, pp. 549-553, 1999.

Seward et al., The Effects of Ethanol, Hexan-1-Ol, and 2-Phenylethanol on Cider Yeast Growth, Viability, and Energy Status; Synergistic Inhibition, Journal of the Institute of Brewin, vol. 102, pp. 439-443, 1996.

Shanmughapriya et al., Synergistic Effect of Amphotericin B and Tyrosol on Biofilm Formed by Candida Krusei and Candida Tropicalis From Intrauterine Device Users, Medical Mycology, vol. 52, pp. 853-861,2014.

Stranks et al., Effect of Phenethyl Alcohol and Other Organic Substances on Cellulas Production, Mycopathologia, vol. 55, No. 1, pp. 57-63, 1975.

Velasco et al., Production of 2-Phenylethanol in the Biotransformation of Cinnamyl Alcohol by the Plant Pathogenic Fungus Colletotrichum Acutatum, Vitae, Revista de la Facultad de Química Farmacéutica, vol. 17, No. 3, pp. 272-280, 2010.

Verma et al., Synergistic Penetration Enhancement Effect of Ethanol and Phospholipids on the Topical Delivery of Cyclosporin A, Journal of Controlled Release, vol. 97, Issue 1, pp. 55-66, 2004.

Wisplinghoff et al., Nosocomial Bloodstream Infections in US Hospitals: Analysis of 24,179 Cases From a Prospective Nationwide Surveillance Study, Clinical Infectious Diseases, vol. 39, No. 3, pp. 309-317, 2004.

Xu et al. Two New Phenylglycol Derivatives Isolated From Syringa Reticulata Var. Mandshurica and Their Antifungal Activities, Chemical and Pharmaceutical Bulletin, vol. 57, No. 8, pp. 863-866, 2009.

Yutaka et al., Antifungal Agent and Antimicrobial Product Using the Same, Abstract, Publication No. 2005035931, Publication Date: Feb. 10, 2005.

Zaoutis et al., The Epidemiology and Attributable Outcomes of Candidemia in Adults and Children Hospitalized in The United States: A Propensity Analysis, Clinical Infectious Diseases, vol. 41, No. 9, pp. 1232-1239, 2005.

Zoric et al., Hydroxytyrosol Expresses Antifungal Activity In Vitro, Current Cancer Drug Targets, vol. 14, No. 9, pp. 992-998, 2013.

(56) References Cited

OTHER PUBLICATIONS

File History of U.S. Appl. No. 15/516,879, accessed on Jul. 14, 2020.
Office Action dated Sep. 6, 2018 in U.S. Appl. No. 15/516,879.
Office Action dated Feb. 15. 2019 in U.S. Appl. No. 15/516,879.
Office Action, dated Jun. 8, 2020, in Israeli Application No. 251588.
Supplemental Search Report dated Sep. 7, 2018 in the European Patent Application No. 15849315.5.
Office Action dated Jan. 23, 2022, in Israeli Application No. 251588.
Office Action dated Dec. 7, 2021 in Canadian Patent Application No. 2,963,923.
Extended European Search Report dated Oct. 21, 2021 in European Application No. EP 21170644.5.

* cited by examiner

METHODS AND COMPOSITIONS FOR INCREASING THE POTENCY OF ANTIFUNGAL AGENTS

CROSS REFERENCE TO RELATED APPLICATIONS

The present application is a Divisional Application of U.S. application Ser. No. 15/516,879, filed on Apr. 4, 2017, which is a U.S. National Phase Application under 35 U.S.C. § 371 of PCT International Application No. PCT/US2015/054304, filed on Oct. 6, 2015, designating the United States of America and published in the English language, which claims the benefit of priority to U.S. Provisional Patent Application No. 62/061,579, entitled METHODS AND COMPOSITIONS FOR INCREASING THE POTENCY OF ANTIFUNGAL AGENTS, filed on Oct. 8, 2014 and U.S. Provisional Patent Application No. 62/190,660, entitled METHODS AND COMPOSITIONS FOR INCREASING THE POTENCY OF ANTIFUNGAL AGENTS, filed on Jul. 9, 2015. The entire disclosures of the aforementioned applications are expressly incorporated herein by reference in their entirety.

FIELD OF THE INVENTION

Embodiments provided herein include methods, compositions, and uses of aromatic alcohols to increase the potency of antifungal agents.

BACKGROUND OF THE INVENTION

Opportunistic fungal pathogens pose a large and growing problem for the U.S. healthcare system. Infection by *Candida* species is the fourth most common cause of hospital-acquired septicemia in the U.S., with mortality rates that range from 5-71% depending on the infecting species (Wisplinghoff, H. et al. (2004) Clin Infect Dis. 39:309-317; Pfaller, M. A. et al., (2007) Clin. Microbiol. Rev. 20:133-163; and Falagas, M. E., et al., (2006) Eur J Clin Microbiol Infect Dis 25:419-425). Long known to target patients with compromised immune systems resulting from disease, HIV/AIDS, chemotherapy, or organ transplantation, invasive fungal infections now plague other susceptible populations. Invasive candidiasis is the second most common cause of death by infection in extreme low birth weight infants. Despite antifungal treatment, 20% of infants who develop invasive candidiasis die, and of those that survive, 60% have some form of neurodevelopmental impairment (Benjamin, D. K., Jr. et al. (2006) Pediatrics 117:84-92). The total direct cost of candidiasis to the U.S. health care system has been estimated at $2-4 billion annually (Zaoutis, T. E. et al. (2005) Clin Infect Dis. 41:1232-1239; Pierce, C. G. et al., (2013) Expert Opinion on Drug Discovery 8:1117-1126). Indeed, antifungal therapy is limited by the small arsenal of drugs, toxicity, and the emergence of resistance. Moreover, the antifungal drug pipeline is mostly dry, so that no new antifungal drugs are expected to reach the market anytime soon. Accordingly, there is a need for additional antifungal therapies.

SUMMARY OF THE INVENTION

Some embodiments of the methods and compositions provided herein include a method of increasing the sensitivity of a fungal cell to an antifungal agent comprising: contacting the cell with phenyl ethanol in combination with the antifungal agent.

Some embodiments of the methods and compositions provided herein include a method of increasing the sensitivity of a fungal cell to an antifungal agent comprising: contacting the cell with a compound of Formula I in combination with the antifungal agent, wherein Formula I is:

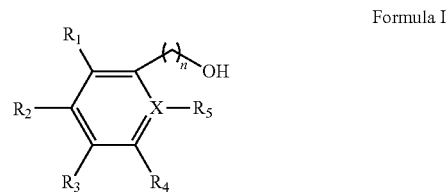

Formula I wherein, X is selected from C, N, S and O; $R_1$-$R_5$ is each independently selected from hydrogen, $C_1$ to $C_6$ alkyl, $C_1$ to $C_6$ substituted alkyl, $C_1$ to $C_6$ alkenyl, $C_1$ to $C_6$ substituted alkenyl; aryl, heteroaryl, alkoxy, and aryloxy; and n is 0, 1, 2, 3, 4, 5 or 6.

In some embodiments, the sensitivity of the cell is increased at least about 2-fold compared to a cell not contacted with phenyl ethanol. In some embodiments, the sensitivity of the cell is increased at least about 5-fold compared to a cell not contacted with phenyl ethanol. In some embodiments, the sensitivity of the cell is increased at least about 20-fold compared to a cell not contacted with phenyl ethanol.

In some embodiments, the cell is selected from the group consisting of *Candida* spp, *Epidermophyton* spp, *Histoplasma* spp, *Trichophyton* spp, *Microsporum* spp, *Blastomyces* spp, *Histoplasma* spp, *Cryptococcus* spp, *Coccidioides* spp *Pneumocystis* spp, *Saccharomyces* spp, *Aspergillus* spp, *Kluyveromyces* spp, *Schizosaccharomyces* spp, and *Streptomyces* spp. In some embodiments, the *Candida* spp is selected from the group consisting of *C. albicans, C. glabrata, C. rugosa, C. parapsilosis, C. tropicalis*, and *C. dubliniensis*. In some embodiments, the *Epidermophyton* spp is *E. floccosum*.

In some embodiments, the antifungal agent is selected from the group consisting of a polyene, an imidazole, a triazole, a thiazole, an allylamine, Sordarin, Flucytosine and an echinocandin. In some embodiments, the polyene is selected from the group consisting of Amphotericin B, Candicidin, Filipin, Hamycin, Natamycin and Rimocidin In some embodiments, the imidazole is selected from the group consisting of Bifonazole, Butoconazole, Clotrimazole, Econazole, Fenticonazole, Isoconazole, Ketoconazole, Luliconazole, Miconazole, Omoconazole, Oxiconazol, Sertaconazole, Sulconazole, and Tioconazole. In some embodiments, the triazole is selected from the group consisting of Albaconazole, Fluconazole, Isavuconazole, Itraconazole, Posaconazole, Ravuconazole, Terconazole, and Voriconazole. In some embodiments, the thiazole comprises Abafungin. In some embodiments, the allylamine is selected from the group consisting of Amorolfin, Butenafine, Naftifine, and Terbinafine. In some embodiments, the echinocandin is selected from the group consisting of Anidulafungin and Micafungin.

Some embodiments of the methods and compositions provided herein include a method of treating and preventing a fungal infection comprising: administering an effective amount of phenyl ethanol in combination with an antifungal agent to a subject in need thereof.

In some embodiments, the subject is mammalian. In some embodiments, the subject is human.

In some embodiments, the subject is suffering from an autoimmune disorder. In some embodiments, the autoimmune disorder is a result of chemotherapy. In some embodiments, the autoimmune disorder is a result of an organ transplant.

In some embodiments, the fungal infection is selected from the group consisting of *Candida* spp, *Epidermophyton* spp, *Histoplasma* spp, *Trichophyton* spp, *Microsporum* spp, *Blastomyces* spp, *Histoplasma* spp, *Cryptococcus* spp, *Coccidioides* spp *Pneumocystis* spp, *Saccharomyces* spp, *Aspergillus* spp, *Kluyveromyces* spp, *Schizosaccharomyces* spp, and *Streptomyces* spp. In some embodiments, the *Candida* spp is selected from the group consisting of *C. albicans, C. glabrata, C. rugosa, C. parapsilosis, C. tropicalis*, and *C. dubliniensis*. In some embodiments, the *Epidermophyton* spp is *E. floccosum*.

in some embodiments, the antifungal agent is selected from the group consisting of a polyene, an imidazole, a triazole, a thiazole, an allylamine, and an echinocandin. In some embodiments, the polyene is selected from the group consisting of Amphotericin B, Candicidin, Filipin, Hamycin, Natamycin, and Rimocidin In some embodiments, the imidazole is selected from the group consisting of Bifonazole, Butoconazole, Clotrimazole, Econazole, Fenticonazole, Isoconazole, Ketoconazole, Luliconazole, Miconazole, Omoconazole, Oxiconazol, Sertaconazole, Sulconazole, and Tioconazole. In some embodiments, the triazole is selected from the group consisting of Albaconazole, Fluconazole, Isavuconazole, Itraconazole, Posaconazole, Ravuconazole, Terconazole, and Voriconazole. In some embodiments, the thiazole comprises Abafungin. In some embodiments, the allylamine is selected from the group consisting of Amorolfin, Butenafine, Naftifine, and Terbinafine. In some embodiments, the echinocandin is selected from the group consisting of Anidulafungin and Micafungin.

Some embodiments of the methods and compositions provided herein include a pharmaceutical composition comprising: phenyl ethanol; an antifungal agent; and a pharmaceutical acceptable carrier. In some embodiments, the phenyl ethanol comprises a concentration of 625 µM to 10 mM.

In some embodiments, the pharmaceutical composition is suitable for topical administration. In some embodiments, the composition is selected from the group consisting of an aerosol, powder, cream, paste, solution, suspension, and gel.

In some embodiments, the pharmaceutical composition is suitable for intravenous administration.

In some embodiments, the antifungal agent is selected from the group consisting of a polyene, an imidazole, a triazole, a thiazole, an allylamine, and an echinocandin. In some embodiments, the polyene is selected from the group consisting of Amphotericin B, Candicidin, Flamycin, Natamycin, and Rimocidin In some embodiments, the imidazole is selected from the group consisting of Bifonazole, Butoconazole, Clotrimazole, Econazole, Fenticonazole, Isoconazole, Ketoconazole, Luliconazole, Miconazole, Omoconazole, Oxiconazol, Sertaconazole, Sulconazole, and Tioconazole. In some embodiments, the triazole is selected from the group consisting of Albaconazole, Fluconazole, Isavuconazole, Itraconazole, Posaconazole, Ravuconazole, Terconazole, and Voriconazole. In some embodiments, the thiazole comprises Abafungin. In some embodiments, the allylamine is selected from the group consisting of Amorolfin, Butenafine, Naftifine, and Terbinafine. In some embodiments, the echinocandin is selected from the group consisting of Anidulafungin and Micafungin.

Some embodiments of the methods and compositions provided herein include a medical device comprising an antifungal coating, wherein the antifungal coating comprises phenyl ethanol. In some embodiments, the antifungal coating further comprises an antifungal agent.

Some embodiments of the methods and compositions provided herein include a method of manufacturing a medical device comprising: coating the medical device with a coating comprising phenyl ethanol and an antifungal agent. In some embodiments, the medical device is selected from the group consisting of a catheter, an endoscope, a laryngoscope, a tube for feeding, a tube for drainage, a tube for endotracheal use, a guide wire, a condom, a glove, a wound dressing, a contact lens, an implant, an extracorporeal blood conduit, a membrane for dialysis, a blood filter, and a device for circulatory assistance.

In some embodiments, the antifungal agent is selected from the group consisting of a polyene, an imidazole, a triazole, a thiazole, an allylamine, and an echinocandin. In some embodiments, the polyene is selected from the group consisting of Amphotericin B, Candicidin, Filipin, Natamycin, and Rimocidin. In some embodiments, the imidazole is selected from the group consisting of Bifonazole, Butoconazole, Clotrimazole, Econazole, Fenticonazole, isoconazole, Ketoconazole, Luliconazole, Miconazole, Omoconazole, Oxiconazol, Sertaconazole, Sulconazole, and Tioconazole. In some embodiments, the triazole is selected from the group consisting of Albaconazole, Fluconazole, Isavuconazole, Itraconazole, Posaconazole, Ravuconazole, Terconazole, and Voriconazole. In some embodiments, the thiazole comprises Abafungin. In some embodiments, the allylamine is selected from the group consisting of Amorolfin, Butenafine, Naftifine, and Terbinafine. In some embodiments, the echinocandin is selected from the group consisting of Anidulafungin and Micafungin.

Some embodiments of the methods and compositions provided herein include a method of screening or testing a composition for fungal targets, the method comprising providing a concentration of phenyl ethanol; providing a concentration of an antifungal agent; and culturing fungal cells under conditions wherein the fungal cells are in contact with the concentration of antifungal agent and the concentration of phenyl ethanol and wherein the fungal cells comprise modified alleles of a gene.

In some embodiments, the gene contributes to the virulence and/or pathogenicity of the fungal cells to a host organism.

In some embodiments, the fungal cells are selected from the group consisting of *Candida* spp, *Epidermophyton* spp, *Histoplasma* spp, *Trichophyton* spp, *Microsporum* spp, *Blastomyces* spp, *Histoplasma* spp, *Cryptococcus* spp, *Coccidioides* spp *Pneumocystis* spp, *Saccharomyces* spp, *Aspergillus* spp, *Kluyveromyces* spp, *Schizosaccharomyces* spp, and *Streptomyces* spp. In some embodiments, the *Candida* spp is selected from the group consisting of *C. albicans, C. glabrata, C. rugosa, C. parapsilosis, C. tropicalis*, and *C. dubliniensis*. In some embodiments, the *Epidermophyton* spp is *E. floccosum*.

In some embodiments, the antifungal agent is selected from the group consisting of a polyene, an imidazole, a triazole, a thiazole, an allylamine, and an echinocandin. In some embodiments, the polyene is selected from the group consisting of Amphotericin B, Candicidin, Filipin, Hamycin, Natamycin, and Rimocidin. In some embodiments, the imidazole is selected from the group consisting of Bifonazole, Butoconazole, Clotrimazole, Econazole, Fenticonazole, Isoconazole, Ketoconazole, Luliconazole, Miconazole, Omoconazole, Oxiconazol, Sertaconazole, Sulconazole, and Tioconazole. In some embodiments, the triazole is selected from the group consisting of Albaconazole, Fluconazole, Isavuconazole, Itraconazole, Posaconazole, Ravuconazole, Terconazole, and Voriconazole. In some embodiments, the thiazole comprises Abafungin. In some embodiments, the allylamine is selected from the group consisting of Amorolfin, Butenafine, Naftifine, and Terbinafine. In some embodiments, the echinocandin is selected from the group consisting of Anidulafungin, and Micafungin.

In some embodiments, a method of increasing the sensitivity of a fungal cell to an antifungal agent is provided wherein the method comprises contacting the cell with an enamine in combination with the antifungal agent. In some embodiments, the sensitivity of the cell is increased at least about 2-fold compared to a cell not contacted with the enamine. In some embodiments, the sensitivity of the cell is increased at least about 5-fold compared to a cell not contacted with the enamine. In some embodiments, the sensitivity of the cell is increased at least about 20-fold compared to a cell not contacted with the enamine. In some embodiments, the cell is selected from the group consisting of *Candida* spp, *Epidermophyton* spp, *Histoplasma* spp, *Trichophyton* spp. *Microsporum* spp, *Blastomyces* spp, *Histoplasma* spp, *Cryptococcus* spp, *Coccidioides* spp *Pneumocystis* spp, *Saccharomyces* spp, *Aspergillus* spp, *Kluyveromyces* spp, *Schizosaccharomyces* spp, and *Streptomyces* spp. In some embodiments, the *Candida* spp is selected from the group consisting of *C. albicans, C. glabrata, C. rugosa, C. parapsilosis, C. tropicalis*, and *C. dubliniensis*. In some embodiments, the *Epidermophyton* spp is *E. floccosum*. In some embodiments, the antifungal agent is selected from the group consisting of a polyene, an imidazole, a triazole, a thiazole, an allylamine, Sordarin, Flucytosine and an echinocandin. In some embodiments, the polyene is selected from the group consisting of Amphotericin B, Candicidin, Filipin, Hamycin, Natamycin and Rimocidin. In some embodiments, the imidazole is selected from the group consisting of Bifonazole, Butoconazole, Clotrimazole, Econazole, Fenticonazole, Isoconazole, Ketoconazole, Luliconazole, Miconazole, Omoconazole, Oxiconazol, Sertaconazole, Sulconazole, and Tioconazole. In some embodiments, the triazole is selected from the group consisting of Albaconazole, Fluconazole, Isavuconazole, Itraconazole, Posaconazole, Ravuconazole, Terconazole, and Voriconazole. In some embodiments, the thiazole comprises Abafungin. In some embodiments, the allylamine is selected from the group consisting of Amorolfin, Butenafine, Naftifine, and Terbinafine. In some embodiments, the echinocandin is selected from the group consisting of Anidulafungin and Micafungin.

In some embodiments, a method of treating and preventing a fungal infection is provided, wherein the method comprises administering an effective amount of an enamine in combination with an antifungal agent to a subject in need thereof. In some embodiments, the subject is mammalian. In some embodiments, the subject is human. In some embodiments, the subject is suffering from an autoimmune disorder. In some embodiments, the autoimmune disorder is a result of chemotherapy. In some embodiments, the autoimmune disorder is a result of an organ transplant. In some embodiments, the fungal infection is selected from the group consisting of *Candida* spp, *Epidermophyton* spp, *Histoplasma* spp, *Trichophyton* spp, *Microsporum* spp, *Blastomyces* spp, *Histoplasma* spp, *Cryptococcus* spp, *Coccidioides* spp *Pneumocystis* spp, *Saccharomyces* spp, *Aspergillus* spp, *Kluyveromyces* spp, *Schizosaccharomyces* spp, and *Streptomyces* spp. In some embodiments, the *Candida* spp is selected from the group consisting of *C. albicans, C. glabrata, C. rugosa, C. parapsilosis, C. tropicalis*, and *C. dubliniensis*. In some embodiments, the *Epidermophyton* spp is *E. floccosum*. In some embodiments, the antifungal agent is selected from the group consisting of a polyene, an imidazole, a triazole, a thiazole, an allylamine, and an echinocandin. In some embodiments, the polyene is selected from the group consisting of Amphotericin B, Candicidin, Filipin, Hamycin, Natamycin and Rimocidin. In some embodiments, the imidazole is selected from the group consisting of Bifonazole, Butoconazole, Clotrimazole, Econazole, Fenticonazole, Isoconazole, Ketoconazole, Luliconazole, Miconazole, Omoconazole, Oxiconazol, Sertaconazole, Sulconazole, and Tioconazole. In some embodiments, the triazole is selected from the group consisting of Albaconazole, Fluconazole, Isavuconazole, Itraconazole, Posaconazole, Ravuconazole, Terconazole, and Voriconazole. In some embodiments, the thiazole comprises Abafungin. In some embodiments, the allylamine is selected from the group consisting of Amorolfin, Butenafine, Naftifine, and Terbinafine. In some embodiments, the echinocandin is selected from the group consisting of Anidulafungin and Micafungin.

In some embodiments, a pharmaceutical composition is provided, wherein the composition comprises an enamine, an antifungal agent and a pharmaceutical acceptable carrier. In some embodiments, the enamine comprises a concentration of 625 uM to 10 mM. In some embodiments, the pharmaceutical composition is suitable for topical administration. In some embodiments, the composition is selected from the group consisting of an aerosol, powder, cream, paste, solution, suspension, and gel. In some embodiments, the pharmaceutical composition is suitable for intravenous administration. In some embodiments, the antifungal agent is selected from the group consisting of a polyene, an imidazole, a triazole, a thiazole, an allylamine, and an echinocandin. In some embodiments, the polyene is selected from the group consisting of Amphotericin B, Candicidin, Filipin, Hamycin, Natamycin and Rimocidin. In some embodiments, the imidazole is selected from the group consisting of Bifonazole, Butoconazole, Clotrimazole, Econazole, Fenticonazole, Isoconazole, Ketoconazole, Luliconazole, Miconazole, Omoconazole, Oxiconazol, Sertaconazole, Sulconazole, and Tioconazole. In some embodiments, the triazole is selected from the group consisting of Albaconazole, Fluconazole, Isavuconazole, Itraconazole, Posaconazole, Ravuconazole, Terconazole, and Voriconazole. In some embodiments, the thiazole comprises Abafungin. In some embodiments, the allylamine is selected from the group consisting of Amorolfin, Butenafine, Naftifine, and Terbinafine. In some embodiments, the echinocandin is selected from the group consisting of Anidulafungin and Micafungin.

In some embodiments, a medical device comprising an antifungal coating is provided, wherein the antifungal coating comprises an enamine. In some embodiments, the antifungal coating further comprises an antifungal agent. In some embodiments, a method of manufacturing a medical device is provided, wherein the method comprises coating the medical device with a coating comprising an enamine and an antifungal agent. In some embodiments, of the medical device or method of manufacturing a medical device, the medical device is selected from the group consisting of a catheter, an endoscope, a laryngoscope, a tube for feeding, a tube for drainage, a tube for endotracheal use, a guide wire, a condom, a glove, a wound dressing, a contact lens, am implant, an extracorporeal blood conduit, a membrane for dialysis, a blood filter, and a device for circulatory assistance. In some embodiments, of the medical device or method of manufacturing a medical device, the antifungal agent is selected from the group consisting of a polyene, an imidazole, a triazole, a thiazole, an allylamine, and an echinocandin. In some embodiments, of the medical device or method of manufacturing a medical device, the polyene is selected from the group consisting of Amphotericin B, Candicidin, Filipin, Hamycin, Natamycin and Rimocidin. In some embodiments, of the medical device or method of manufacturing a medical device, the imidazole is selected from the group consisting of Bifonazole, Butoconazole, Clotrimazole, Econazole, Fenticonazole, Isoconazole, Ketoconazole, Luliconazole, Miconazole, Omoconazole, Oxiconazol, Sertaconazole, Sulconazole, and Tioconazole. In some embodiments, of the medical device or method of manufacturing a medical device, the triazole is selected from the group consisting of Albaconazole, Fluconazole, Isavuconazole, Itraconazole, Posaconazole, Ravuconazole, Terconazole, and Voriconazole. In some embodiments, of the medical device or method of manufacturing a medical device, the thiazole comprises Abafungin. In some embodiments, of the medical device or method of manufacturing a medical device, the allylamine is selected from the group consisting of Amorolfin, Butenafine, Naftifine, and Terbinafine. In some embodiments, of the medical device or method of manufacturing a medical device, the echinocandin is selected from the group consisting of Anidulafungin and Micafungin.

In some embodiments, a method of screening or testing a composition for fungal targets is provided, the method comprising providing a concentration of an enamine, providing a concentration of an antifungal agent, and culturing fungal cells under conditions wherein the fungal cells are in contact with the concentration of antifungal agent and the concentration of an enamine and wherein the fungal cells comprise modified alleles of a gene. In some embodiments, the gene contributes to the virulence and/or pathogenicity of the fungal cells to a host organism. In some embodiments, the fungal cells are selected from the group consisting of *Candida* spp, *Epidermophyton* spp, *Histoplasma* spp, *Trichophyton* spp, *Microsporum* spp, *Blastomyces* spp, *Histoplasma* spp, *Cryptococcus* spp, *Coccidioides* spp *Pneumocystis* spp, *Saccharomyces* spp, *Aspergillus* spp, *Kluyveromyces* spp, *Schizosaccharomyces* spp, and *Streptomyces* spp. In some embodiments, the *Candida* spp is selected from the group consisting of *C. albicans, C. glabrata, C. rugosa, C. parapsilosis, C. tropicalis,* and *C. dubliniensis*. In some embodiments, the *Epidermophyton* spp is *E. floccosum*. In some embodiments, the antifungal agent is selected from the group consisting of a polyene, an imidazole, a triazole, a thiazole, an allylamine, and an echinocandin. In some embodiments, the polyene is selected from the group consisting of Amphotericin B, Candicidin, Filipin, Hamycin, Natamycin and Rimocidin. In some embodiments, the imidazole is selected from the group consisting of Bifonazole, Butoconazole, Clotrimazole, Econazole, Fenticonazole, Isoconazole, Ketoconazole, Luliconazole, Miconazole, Omoconazole, Oxiconazol, Sertaconazole, Sulconazole, and Tioconazole. In some embodiments, the triazole is selected from the group consisting of Albaconazole, Fluconazole, Isavuconazole, Itraconazole, Posaconazole, Ravuconazole, Terconazole, and Voriconazole. In some embodiments, the thiazole comprises Abafungin. In some embodiments, the allylamine is selected from the group consisting of Amorolfin, Butenafine, Naftifine, and Terbinafine. In some embodiments, the echinocandin is selected from the group consisting of Anidulafungin and Micafungin.

BRIEF DESCRIPTION OF THE DRAWINGS

(FIG. 2, panel A) Wild-type F45 shows a level of sensitivity to FLU and that sensitivity is increased (larger zone of growth inhibition) in the presence of 10 mM PE. (FIG. 2, panel B) The F45 flo11Δ mutant displays the same levels of FLU sensitivity, i.e. the same sized growth inhibition zones, as wild-type for both the FLU alone and FLU+PE condition.

DEFINITIONS

Figure 1:
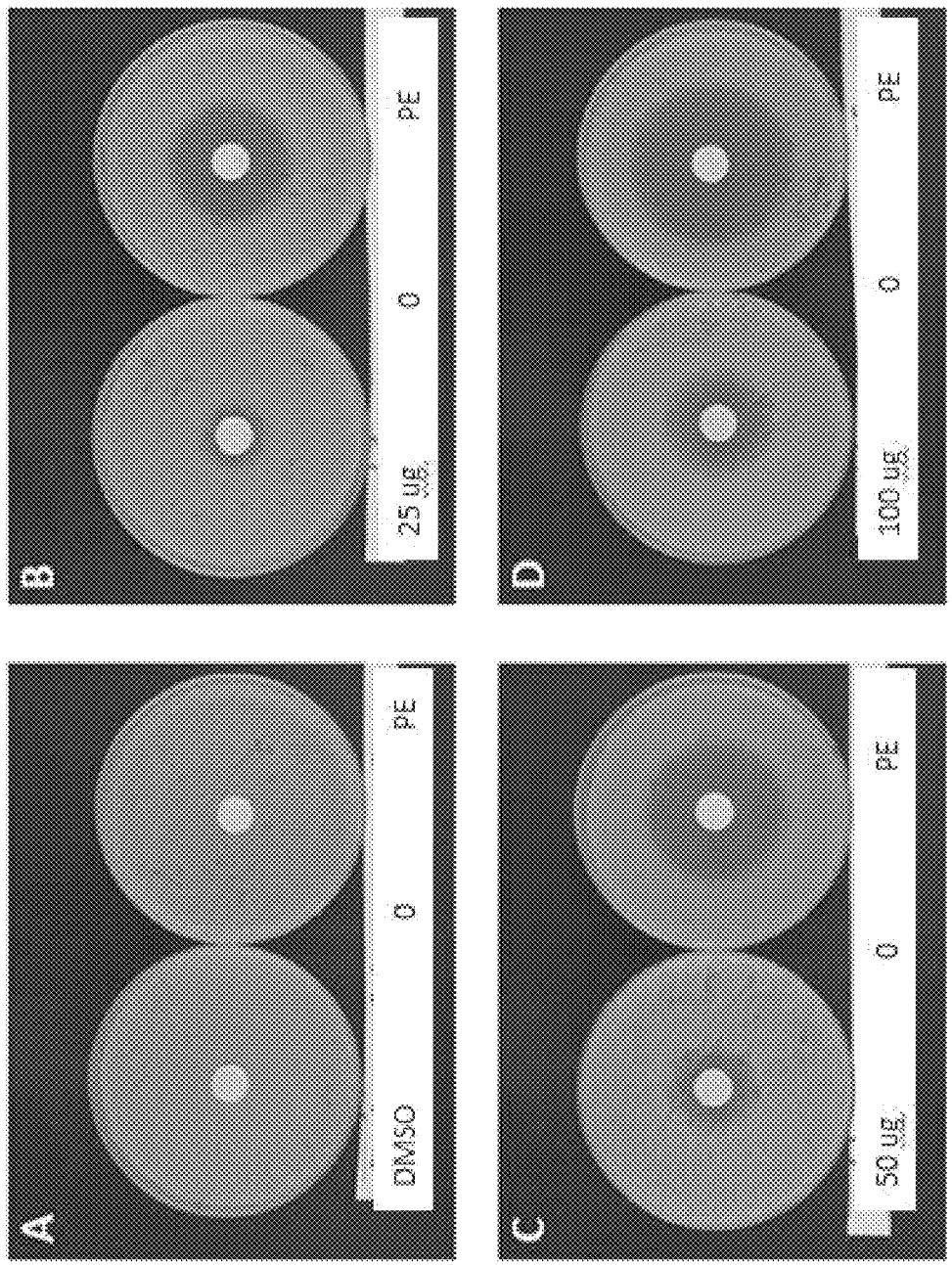
FIG. 1 (panels A-D) shows photographs of a plate assay showing the effects of PE and an antifungal drug on the yeast, *Saccharomyces cerevisiae*. Each panel (panel A-D) shows 2 YPD plates spread with a lawn of *S. cerevisiae* (F45). In each panel, the left plate is YPD alone and the right plate is YPD plus 10 mM PE (a concentration that inhibits the fluffy colony morphology). Each plate also contains a paper disk containing the DMSO vehicle (FIG. 1, panel A), 25 μg fluconazole (FIG. 1, panel B), 50 μg fluconazole (FIG. 1, panel C), or 100 μg fluconazole (FIG. 1, panel D).

As described herein, increasing the sensitivity of a drug or an antifungal refers to increasing the potency of a drug/antifungal, increasing the activity of the drug/antifungal, decreasing the time of the drug/antifungal to perform the therapeutic effect, and/or increase the efficacy of the drug/antifungal.

"Antifungal agents" as described herein refers to an agent that can be used to treat, ameliorate and/or prevent a fungal growth. Without being limiting, examples of antifungal agents can include, for example, fluconazole, voroconazole, itraconazole, flucytosine, sordarin, caspofungin and nystatin.

"Autoimmune disorder," as described herein, refers to a disease that arises from an abnormal immune response of the body against substances and tissues normally present in the body. Without being limiting, autoimmune diseases can include myocarditis, postmyocardial infarction syndrome, Postpericardiotomy syndrome, Subacute bacterial endocarditis, Anti-Glomerular Basement Membrane nephritis, Interstitial cystitis, Lupus nephritis, Autoimmune hepatitis, Primary biliary cirrhosis, Primary sclerosing cholangitis, Antisynthetase syndrome, Antisynthetase syndrome, Alopecia Areata, Autoimmune Angioedema, Autoimmune Angioedema, Autoimmune progesterone dermatitis, Autoimmune urticarial, Bullous pemphigoid, Cicatricial pemphigoid, Dermatitis herpetiformis, Discoid lupus erythematosus, Epidermolysis bullosa acquisita, Erythema nodosum, Gestational pemphigoid, Hidradenitis suppurativa, Lichen planus, Lichen sclerosus, Linear IgA disease, Morphea, Pemphigus vulgaris, Pityriasis lichenoides et varioliformis acuta, Mucha-Habermann disease, Psoriasis, Systemic scleroderma, Vitiligo, Addison's disease, Autoimmune polyendocrine syndrome, Autoimmune polyendocrine syndrome type 2, Autoimmune polyendocrine syndrome type 3, Autoimmune pancreatitis, Diabetes mellitus type 1, Autoimmune thyroidit, Ord's thyroiditis, Graves' disease, Autoimmune oophoritis, Endometriosis, Autoimmune orchitis, Sjogren's syndrome, Autoimmune enteropathy, Celiac disease, Crohn's disease, Microscopic colitis, Ulcerative colitis, Antiphospholipid syndrome, Aplastic anemia, Autoimmune hemolytic anemia, Autoimmune lymphoproliferative syndrome, Autoimmune neutropenia, Autoimmune thrombocytopenic purpura, Cold agglutinin disease, Essential mixed cryoglobulinemia, Evans syndrome, IgG4-related systemic disease, Paroxysmal nocturnal hemoglobinuria, Pernicious anemia, Pure red cell aplasia, Thrombocytopenia, Adiposis dolorosa, Adult-onset Still's disease, Ankylosing Spondylitis, CREST syndrome, Drug-induced lupus, Enthesitis-related arthritis, Eosinophilic fasciitis, Felty syndrome, Juvenile Arthritis, Lyme disease (Chronic), Mixed connective tissue disease, Palindromic rheumatism, Parry Romberg syndrome, Parsonage-Turner syndrome, Psoriatic arthritis, Reactive arthritis, Relapsing polychondritis, Retroperitoneal fibrosis, Rheumatic fever, Rheumatoid arthritis, Sarcoidosis, Schnitzler syndrome, Systemic Lupus Erythematosus, Undifferentiated connective tissue disease, Dermatomyositis, Fibromyalgia, Inclusion body myositis, Myositis, Myasthenia gravis, Neuromyotonia, Paraneoplastic cerebellar degeneration, Polymyositis, Acute disseminated encephalomyelitis, Acute motor axonal neuropathy, Anti-N-Methyl-D-Aspartate Receptor Encephalitis, Balo concentric sclerosis, Bickerstaff's encephalitis, Chronic inflammatory demyelinating polyneuropathy, Guillain-Barré syndrome, Hashimoto's encephalopathy, Idiopathic inflammatory demyelinating diseases, Lambert-Eaton myasthenic syndrome, Multiple sclerosis, Narcolepsy, Pediatric Autoimmune Neuropsychiatric Disorder Associated with Streptococcus, Progressive inflammatory neuropathy, Restless leg syndrome, Stiff person syndrome, Sydenham chorea, Transverse myelitis, Autoimmune retinopathy, Autoimmune uveitis, Cogan syndrome, Graves ophthalmopathy, Graves ophthalmopathy, intermediate uveitis, Anti-neutrophil cytoplasmic antibody-associated vasculitis, Kawasaki's disease, Leukocytoclastic vasculitis, Lupus vasculitis, and Rheumatoid vasculitis.

Chemotherapy can also lead to an increase in autoimmune disorder or can decrease the immune response. Additionally, an autoimmune disorder can result from an organ transplant or drugs for immune suppression.

DETAILED DESCRIPTION

Commonly used antifungal drugs target just two cellular components, ergosterol in the plasma membrane and 1,3-beta-D-glucan in the cell wall. Drugs that target ergosterol include the commonly used triazoles (e.g. fluconazole) and formulations of the polyene Amphotericin B, reserved as a last line of defense due to its toxicity (Ostrosky-Zeichner, L., et al., (2010) Nature Reviews Drug discovery 9: 719-727). Echinocandins have the advantage of attacking a fungal specific target, 1,3-beta-D-glucan synthase activity which weakens the fungal cell wall. However, drug resistant mutations in FKS1 that prevent echinocandin binding are an increasing problem (Alexander, B. D. et al. (2013) Clin Infect Dis. 56:1724-1732).

Benzyl alcohol is an aromatic alcohol with the formula $C_6H_5CH_2OH$ and can be used for disrupting colonies of certain fungi. In some embodiments, the presence of a benzyl alcohol or its derivative can disrupt structured colony morphology of certain fungi. In some embodiments of the methods and compositions provided herein, the presence of phenyl ethanol (PE) or its derivatives can disrupt structured colony morphology of certain fungi, such as *Saccharomyces cerevisiae*. In some embodiments, PE or its derivatives can increase the sensitivity of yeast cells to antifungals. In some embodiments, PE or its derivatives can destroy biofilms. In some embodiments, a benzyl alcohol or its derivatives can increase the sensitivity of yeast cells to antifungals. In some embodiments, benzyl alcohol or its derivatives can destroy biofilms.

In some embodiments provided herein, PE or its derivatives can be used to increase the sensitivity of yeast to antifungal drugs, can increase the efficacy of antifungal drugs, can lower the dose of drugs needed, thereby decreasing adverse effects of drugs with significant toxicity), and the compound (or some chemical with similar properties or activities) can be used as a surface coating for medical devices. PE and its' derivatives can be used for treating and preventing fungal infections in subjects that are immunocompromised. In some embodiments, PE can be chemically linked to antifungal drugs. In some embodiments, PE increases the efficacy of antifungal drugs. In some embodiments, PE enhances the sensitivity of *S. cerevisiae* to Voriconazole. In some embodiments, PE enhances the sensitivity of yeast to Voriconazole. In some embodiments, PE enhances the sensitivity of *S. cerevisiae* to Itraconazole. In some embodiments, PE enhances the sensitivity of yeast to Itraconazole. In some embodiments, PE enhances the sensitivity of *S. cerevisiae* to Sordarin. In some embodiments, PE enhances the sensitivity of yeast to Sordarin. In some embodiments, PE increases the efficacy of specific antifungal drugs in pathogenic fungi. In some embodiments, PE increases the efficacy of triazoles against pathogenic fungi. In some embodiments, PE increases the efficacy of fluconazole against *C. albicans*. In some embodiments, PE increases the efficacy of fluconazole against yeast. In some embodiments, PE increases the efficacy of fluconazole against *C. albicans* strains. In some embodiments, PE increases the efficacy of flucytosine against *C. albicans*. In some embodiments, PE increases the efficacy of flucytosine against yeast. Additional embodiments regarding the PE to increase efficacy to antifungal drugs are provided herein.

Phenyl Ethanol and Derivatives

Some embodiments of the methods and compositions provide herein include the use of phenyl ethanol and derivatives thereof. In some embodiments, the phenyl ethanol derivative has the below structure of Formula I:

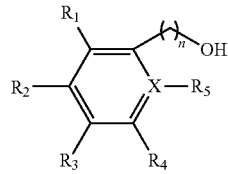

Formula I wherein X is selected from C, N, S and O;
$R_1$-$R_5$ is each independently selected from hydrogen, $C_1$ to $C_6$ alkyl, $C_1$ to $C_6$ substituted alkyl, $C_1$ to $C_6$ alkenyl, $C_1$ to $C_6$ substituted alkenyl; aryl, heteroaryl, alkoxy, and aryloxy; and
n is 0, 1, 2, 3, 4, 5 or 6.

Some embodiments relate to phenyl ethanol (PE) which has the following structure:

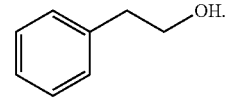

Antifungal Agents

Some embodiments of the methods and compositions provide herein include an antifungal agent. In some embodiments, the antifungal agent is selected from the group consisting of a polyene, an imidazole, a triazole, a thiazole, an allylamine, and an echinocandin. In some embodiments, the polyene is selected from the group consisting of Amphotericin B, Candicidin, Filipin, Hamycin, Natamycin, Nystatin, Flucytosine, Sordarin and Rimocidin. In some embodiments, the imidazole is selected from the group consisting of Bifonazole, Butoconazole, Clotrimazole, Econazole, Fenticonazole, Isoconazole, Ketoconazole, Luliconazole, Miconazole, Omoconazole, Oxiconazol, Sertaconazole, Sulconazole, and Tioconazole. In some embodiments, the triazole is selected from the group consisting of Albaconazole, Fluconazole, Isavuconazole, Itraconazole, Posaconazole, Ravuconazole, Terconazole, and Voriconazole. In some embodiments, the thiazole comprises Abafungin. In some embodiments, the allylamine is selected from the group consisting of Amorolfin, Butenafine, Naftifine, and Terbinafine. In some embodiments, the echinocandin is selected from the group consisting of Anidulafungin, Caspofungin, and Micafungin.

Fungal Cells and Infections

Some embodiments of the methods and compositions provide herein include fungal cells, biofilms, filamentous forms of such cells, and multicellular forms of such cells. In some embodiments, the fungus can include a genus selected from *Candida* spp, *Epidermophyton* spp, *Histoplasma* spp, *Trichophyton* spp, *Microsporum* spp, *Blastomyces* spp, *Histoplasma* spp, *Cryptococcus* spp, *Coccidioides* spp, *Pneumocystis* spp, *Saccharomyces* spp, *Aspergillus* spp, *Kluyveromyces* spp, *Schizosaccharomyces* spp, and *Streptomyces* spp. In some embodiments, the *Candida* spp can include *C. albicans, C. glabrata, C. rugosa, C. parapsilosis,*

*C. tropicalis*, and *C. dubliniensis*. In some embodiments, the *Epidermophyton* spp is *E. floccosum*.

Medical Devices

Without being limiting, medical devices can include, for example, an instrument, apparatus, implant, in vitro reagent or similar article that can be used to diagnose, prevent or treat disease or other conditions in a subject in need. These can include, for example, tongue depressors, thermometers, gloves, needles, surgical instruments and other devices for medical testings, implants, and prosthetics. Some embodiments of the methods and compositions provide herein include a medical device comprising an antifungal coating, wherein the antifungal coating comprises phenyl ethanol and an antifungal agent. In some embodiments, the medical device can include a catheter, an endoscope, a laryngoscope, a tube for feeding, a tube for drainage, a tube for endotracheal use, a guide wire, a condom, a glove, a wound dressing, a contact lens, an implant, an extracorporeal blood conduit, a membrane for dialysis, a blood filter, a heart valve, pace makers, artificial joints (i.e., hips, knees, etc) and a device for circulatory assistance (i.e., pace maker, Dacron valve, etc).

Some embodiments of the methods and compositions provide herein include manufacturing a medical device comprising coating the medical device with a coating comprising phenyl ethanol and an antifungal agent.

Increasing the Potency of Antifungal Agents

Some embodiments of the methods and compositions provide herein include treating and preventing a fungal infection with an antifungal agent in combination with phenyl ethanol. In some embodiments, the method further comprises administering an effective amount of phenyl ethanol in combination with an antifungal agent to a subject in need thereof. In some such embodiments, the antifungal agent and phenyl ethanol can be administered in a single composition, in separate compositions, simultaneously, or sequentially such that the antifungal agent and phenyl ethanol have a synergistic effect. Some embodiments of the methods and compositions provide herein include increasing the sensitivity of a fungal cell to an antifungal agent comprising contacting the cell with an antifungal agent in combination with phenyl ethanol. In some embodiments, a composition is provided. In the broadest sense, the composition can comprise PE and an antifungal agent. In some embodiments, the composition can comprise PE, wherein the PE is covalently linked to an antifungal agent. In some such embodiments, the cell can be contacted with the antifungal agent and phenyl ethanol in a single composition, in separate compositions, simultaneously, or sequentially such that the antifungal agent and phenyl ethanol have a synergistic effect. In some embodiments, a cream is provided. In the broadest sense, the cream can comprise a composition of any of the embodiments described herein.

Screening for New Drug Targets

Screening for drug targets can involve introducing fungal strains to a concentration of PE and an antifungal agent during culturing of the fungal cells. During a culture process susceptibility is performed on the fungi. The pathogenic fungi can be tested to determine the ability of an antifungal agent or a composition comprising an antifungal agent to inhibit its growth. As such as screen can be performed that can measure directly the effects of an antifungal agent or a composition thereof, by bringing the pathogenic fungal target and the antifungal agent together in a growing environment such as a nutrient media in a test tube or an agar plate to observe the effects of the agent on the growth of the fungal target. Sensitivity to an anti-fungal agent can be observed by the lack of growth of the fungal target. In some embodiments, a method of screening or testing a composition for fungal targets is contemplated. In some embodiments, the method comprises providing a concentration of PE, providing a concentration of an antifungal agent, culturing fungal cells under conditions wherein the fungal cells are in contact with the concentration of antifungal agent and the concentration of PE and wherein the fungal cells comprise modified alleles of a gene, and screening for cells sensitive to the concentration of PE and the concentration of the antifungal agent, wherein screening comprises assaying the fungal cells for growth. In some embodiments, the gene is essential for the growth and/or survival of the fungal cells. In some embodiments, the gene contributes to the virulence and/or pathogenicity of the fungal cells to a host organism. In some embodiments, the genes are for echinocandin binding. In some embodiments, the fungal cells are selected from the group consisting of *Candida* spp, *Epidermophyton* spp, *Histoplasma* spp, *Trichophyton* spp, *Microsporum* spp, *Blastomyces* spp, *Histoplasma* spp, *Cryptococcus* spp, *Coccidioides* spp *Pneumocystis* spp, *Saccharomyces* spp, *Aspergillus* spp, *Kluyveromyces* spp, *Schizosaccharomyces* spp, and *Streptomyces* spp. In some embodiments, the *Candida* spp is selected from the group consisting of *C. albicans, C. glabrata, C. rugosa, C. parapsilosis, C. tropicalis*, and *C. dubliniensis*. In some embodiments, the *Epidermophyton* spp is *E. floccosum*. In some embodiments, the antifungal agent is selected from the group consisting of a polyene, an imidazole, a triazole, a thiazole, an allylamine, and an echinocandin. In some embodiments, the polyene is selected from the group consisting of Amphotericin B, Candicidin, Filipin, Hamycin, Natamycin, Nystatin, and Rimocidin. In some embodiments, the imidazole is selected from the group consisting of Bifonazole, Butoconazole, Clotrimazole, Econazole, Fenticonazole, Isoconazole, Ketoconazole, Luliconazole, Miconazole, Omoconazole, Oxiconazol, Sertaconazole, Sulconazole, and Tioconazole. In some embodiments, the triazole is selected from the group consisting of Albaconazole, Fluconazole, Isavuconazole, Itraconazole, Posaconazole, Ravuconazole, Terconazole, and Voriconazole. In some embodiments, the thiazole comprises Abafungin. In some embodiments, the allylamine is selected from the group consisting of Amorolfin, Butenafine, Naftifine, and Terbinafine. In some embodiments, the echinocandin is selected from the group consisting of Anidulafungin, Caspofungin, and Micafungin.

Pharmaceutical Compositions

In some embodiments, compositions comprise an antifungal agent and phenyl ethanol or derivatives thereof. In some embodiments, the composition comprises an antifungal agent, wherein the antifungal agent is selected from the group consisting of a polyene, an imidazole, a triazole, a thiazole, an allylamine, and an echinocandin. In some embodiments, the polyene is selected from the group consisting of Amphotericin B, Candicidin, Filipin, Hamycin, Natamycin, Nystatin, and Rimocidin. In some embodiments, the imidazole is selected from the group consisting of Bifonazole, Butoconazole, Clotrimazole, Econazole, Fenticonazole, Isoconazole, Ketoconazole, Luliconazole, Miconazole, Omoconazole, Oxiconazol, Sertaconazole, Sulconazole, and Tioconazole. In some embodiments, the triazole is selected from the group consisting of Albaconazole, Fluconazole, Isavuconazole, Itraconazole, Posaconazole, Ravuconazole, Terconazole, and Voriconazole. In some embodiments, the thiazole comprises Abafungin. In some embodiments, the allylamine is selected from the group consisting of Amorolfin, Butenafine, Naftifine, and Terbinafine. In some embodiments, the echinocandin is selected from the group consisting of Anidulafungin, Caspofungin, and Micafungin.

In some embodiments, the active ingredients and mixtures of active ingredients may be used, for example, in pharmaceutical compositions comprising a pharmaceutically acceptable carrier prepared for storage and subsequent administration. Also, some embodiments include use of the above-described active ingredients with a pharmaceutically acceptable carrier or diluent. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, and dyes may be provided in the pharmaceutical composition. For example, sodium benzoate, ascorbic acid and esters of p-hydroxybenzoic acid may be added as preservatives. In addition, antioxidants and suspending agents may be used. In some embodiments the composition comprises preservatives, stabilizers and/or dyes. In some embodiments, the preservatives are selected from a group consisting of sodium benzoate, ascorbic acid and esters of p-hydroxybenzoic acid. In some embodiments, the composition comprises antioxidants. In some embodiments, the composition comprises suspending agents.

Compositions of the active ingredients may be formulated and used as tablets, capsules, or elixirs for oral administration; suppositories for rectal administration; sterile solutions, suspensions for injectable administration; patches for transdermal administration, and sub-dermal deposits and the like. Injectables can be prepared in conventional forms, either as liquid solutions or suspensions, solid forms suitable for solution or suspension in liquid, prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (for example, liposomes), may be utilized. In some embodiments the composition comprises an excipient. In some embodiments the excipient is selected from a group consisting of water, saline, dextrose, mannitol, lactose, lecithin, albumin, sodium glutamate, cysteine hydrochloride, and the like.

For injection, the agents of the invention may be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art. Use of pharmaceutically acceptable carriers to formulate the ingredients herein disclosed for the practice of the invention into dosages suitable for systemic administration is within the scope of the invention. With proper choice of carrier and suitable manufacturing practice, the compositions disclosed herein, in particular, those formulated as solutions, may be administered parenterally, such as by intravenous injection. The active ingredients can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated. In some embodiments, the compositions are formulated as tablets, pills, capsules, liquids, gels, syrups, slurries or suspensions for oral ingestion by the patient in need.

Pharmaceutical formulations for parenteral administration include aqueous solutions of the active ingredients in water-soluble form. Additionally, suspensions of the active ingredients may be prepared as appropriate only injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the ingredients to allow for the preparation of highly concentrated solutions. In some embodiments, the composition is formulated as a suspension. In some embodiments, the suspension is an oily suspension comprising lipophilic solvents or vehicles. In some embodiments, the lipophilic solvents or vehicles comprise fatty oils such as sesame oil, or other organic oils such as soybean, grapefruit or almond oils, or synthetic fatty acid esters, such as ethyl oleate or triglycerides, or liposomes.

Pharmaceutical preparations for oral use can be obtained by combining the active ingredients with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active ingredient doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active ingredient doses. Such formulations can be made using methods known in the art. See, for example, U.S. Pat. No. 5,733,888 (injectable compositions); U.S. Pat. No. 5,726,181 (poorly water soluble compounds); U.S. Pat. No. 5,707,641 (therapeutically active proteins or peptides); U.S. Pat. No. 5,667,809 (lipophilic agents); U.S. Pat. No. 5,576,012 (solubilizing polymeric agents); U.S. Pat. No. 5,707,615 (anti-viral formulations); U.S. Pat. No. 5,683,676 (particulate medicaments); U.S. Pat. No. 5,654,286 (topical formulations); U.S. Pat. No. 5,688,529 (oral suspensions); U.S. Pat. No. 5,445,829 (extended release formulations); U.S. Pat. No. 5,653,987 (liquid formulations); U.S. Pat. No. 5,641,515 (controlled release formulations) and U.S. Pat. No. 5,601,845 (spheroid formulations); all of which are incorporated herein by reference in their entireties. The pharmaceutical compositions may be manufactured in a manner that is itself known, for example, by means of conventional mixing, dissolving, granulating, dragee-making, levitating, emulsifying, encapsulating, entrapping, or lyophilizing processes.

In some embodiments herein the composition for oral use is provided. In some embodiments, the composition for oral use comprises excipients, wherein the excipients are selected from a group consisting of sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). In some embodiments, the composition comprises concentrated sugar solutions, wherein the concentrated sugar solutions are selected from a group consisting of gum arabic, talc, polyvinyl pyrrolidone, carbopol gel, polyethylene glycol, and/or titanium dioxide, lacquer solutions, and suitable organic solvents and solvent mixtures.

To formulate the dosage including one or more active ingredients disclosed herein, known surface active agents, excipients, smoothing agents, suspension agents and pharmaceutically acceptable film-forming substances and coating assistants, and the like may be used. Preferably alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents. In addition to the foregoing ingredients, sweeteners, fragrances, colorants, preservatives and the like may be added to the administered formulation of the compound of the invention, particularly when the compound is to be administered orally. In some embodiments, the composition comprises active ingredients. In some embodiments, the active ingredients are selected from a group consisting of alcohols, esters, and sulfated aliphatic alcohols. In some embodiments, the composition further comprises excipients. In some embodiments, the excipients comprise sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like. In some embodiments, the composition comprises suspension agents and/or lubricants. In some embodiments, the suspension agents and/or lubricants comprise magnesium stearate, talc, hardened oil and the like may be used as smoothing agents; coconut oil, olive oil, sesame oil, peanut oil or soya. In some embodiments, the composition comprises suspension agents. In some embodiments, the suspension agent comprises cellulose acetate phthalate, derivatives of a carbohydrate such as cellulose or sugar, or methylacetate-methacrylate copolymer as a derivative of polyvinyl. In some embodiments, the composition comprises plasticizers. In some embodiments, the plasticizers comprise ester phthalates.

Further disclosed herein are various pharmaceutical compositions well known in the pharmaceutical art for uses that include intraocular, intranasal, and intraauricular delivery. Pharmaceutical formulations include aqueous ophthalmic solutions of the active ingredients in water-soluble form, such as eyedrops, or in gellan gum (Shedden et al., Clin. Ther., 23(3):440-50 (2001)) or hydrogels (Mayer et al., Ophthalmologica, 210(2):101-3 (1996)); ophthalmic ointments; ophthalmic suspensions, such as microparticulates, drug-containing small polymeric particles that are suspended in a liquid carrier medium (Joshi, A., J. Ocul. Pharmacol., 10(1):29-45 (1994)), lipid-soluble formulations (Alm et al., Prog. Clin. Biol. Res., 312:447-58 (1989)), and microspheres (Mordenti, Toxicol. Sci., 52(1):101-6 (1999)); and ocular inserts. All of the above-mentioned references are incorporated herein by reference in their entireties. Such suitable pharmaceutical formulations are most often and preferably formulated to be sterile, isotonic and buffered for stability and comfort. Pharmaceutical compositions may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compositions described herein may be administered by either oral or non-oral pathways. When administered orally, compositions can be administered in capsule, tablet, granule, spray, syrup, or other such form. Compositions also may be brewed, as with a tea, or formed by dissolving a powdered composition into a fluid, typically water, fruit or vegetable juice, or milk. When administered non-orally, it can be administered as an aqueous suspension, an oily preparation or the like or as a drip, suppository, salve, ointment or the like, when administered via injection, subcutaneously, intraperitoneally, intravenously, intramuscularly, or the like. Similarly, it may be administered topically, rectally, or vaginally, as deemed appropriate by those of skill in the art for bringing the ingredients of the invention into optimal contact with living tissue. In some embodiments, wherein the compositions are administered non-orally, the compositions are administered as an aqueous suspension, an oily preparation or the like or as a drip, suppository, salve or ointment. In some embodiments, wherein the composition is administered via injection, the composition is administered subcutaneously, intraperitoneally, intravenously or intramuscularly.

Agents intended to be administered intracellularly may be administered using techniques well known to those of ordinary skill in the art. For example, such agents may be encapsulated into liposomes, then administered by any of the methods described herein. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. Additionally, due to their hydrophobicity, small organic molecules may be directly administered intracellularly.

In some embodiments, the compositions described herein are formulated into a single pill or tablet. In some embodiments, the pill or tablet has a mass from 10 mg to 2000 mg. In some embodiments, the pill or tablet has a mass from 100 mg to 1500 mg. In some embodiments, the pill or tablet has a mass from 500 mg to 1200 mg. In some embodiments, the pill or tablet has a mass from 800 mg to 1100 mg.

Methods of Administration

Some embodiments also encompass methods for making and for administering the disclosed compositions. Such disclosed methods include, among others, (a) administration through oral pathways, which administration includes administration in capsule, tablet, granule, spray, syrup, or other such forms; (b) administration through non-oral pathways, which administration includes administration as an aqueous suspension, an oily preparation or the like or as a drip, suppository, salve, ointment or the like; administration via injection, subcutaneously, intraperitoneally, intravenously, intramuscularly, intradermally, or the like; as well as (c) administration topically, (d) administration rectally, or (e) administration vaginally, as deemed appropriate by those of skill in the art for bringing the compound of the invention into contact with living tissue; and (f) administration via controlled released formulations, depot formulations, and infusion pump delivery. As further examples of such modes of administration and as further disclosure of modes of administration, disclosed herein are various methods for administration of the disclosed compositions including modes of administration through intraocular, intranasal, and intraauricular pathways.

The pharmaceutically effective amount of the ingredients disclosed herein required as a dose will dependent on the route of administration and the physical characteristics of the specific human under consideration. The dose can be tailored to achieve a desired effect, but will depend on such factors as weight, diet, concurrent medication and other factors, which those skilled in the medical arts will recognize.

In practicing the methods of the invention, the products or compositions can be used alone or in combination with one another or in combination with other therapeutic or diagnostic agents. These products can be utilized in vivo, ordinarily in a mammal, preferably in a human, or in vitro. In employing them in vivo, the products or compositions can be administered to the mammal in a variety of ways, including parenterally, intravenously, subcutaneously, intramuscularly, colonically, rectally, vaginally, nasally or intraperitoneally, employing a variety of dosage forms. Such methods may also be applied to testing chemical activity in vivo.

As will be readily apparent to one skilled in the art, the useful in vivo dosage to be administered, the particular mode of administration, and duration of treatment will vary depending upon the age, weight and mammalian species treated, the particular ingredients employed, and the specific use for which these ingredients are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods. In non-human animal studies, applications of potential products are commenced at higher dosage levels, with dosage being decreased until the desired effect is no longer achieved or adverse side effects disappear.

The dosage of active ingredient(s) may range broadly, depending upon the desired affects and the therapeutic indication. Typically, dosages of active ingredient(s) may be between about 10 µg/kg and 100 mg/kg body weight, preferably between about 100 µg/kg and 10 mg/kg body weight. Alternatively dosages may be based and calculated upon the surface area of the patient, as understood by those of skill in the art. Administration is preferably oral on a daily or twice daily basis. In some embodiments, the dosage of the active ingredient is between about 10 µg/kg and 100 mg/kg body weight, or preferably between about 100 µg/kg and 10 mg/kg body weight. In some embodiments, the dosage is administered orally once or twice a day.

The exact formulation, route of administration and dosage can be chosen in view of the consumer's condition. See for example, Fingl et al., in The Pharmacological Basis of Therapeutics, 1975, which is incorporated herein by reference in its entirety. The magnitude of an administrated dose may vary with the severity of a particular medical or physical condition and the route of administration. The severity of a condition may, for example, be evaluated, in part, by standard prognostic evaluation methods. Further, the dose and perhaps dose frequency may also vary according to the age, body weight, and response of the individual. A program comparable to that discussed above may be used in veterinary medicine.

A variety of techniques for formulation and administration may be found in Remington's Pharmaceutical Sciences, 18th Ed., Mack Publishing Co., Easton, Pa. (1990), which is incorporated herein by reference in its entirety. Suitable administration routes may include oral, rectal, intravenous, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, intraocular injections or any other administration route known in the art. In some embodiments, the dosages of the composition is administered though administration routes which can include oral, rectal, intravenous, transdermal, vaginal, transmucosal, or intestinal administration; parenteral delivery, including intramuscular, subcutaneous, intramedullary injections, as well as intrathecal, direct intraventricular, intravenous, intraperitoneal, intranasal or intraocular injections.

The combined active ingredients in the compositions disclosed herein may be orally or non-orally administered to a human patient in the amount of about 0.0007 mg/day to about 7,000 mg/day of the total active ingredients, and more preferably about 0.07 mg/day to about 70 mg/day of the total active ingredients at, one time per day or in other embodiments, over two to about ten times per day. Alternatively, the active ingredients disclosed herein may be administered in the stated amounts continuously by, for example, an intravenous drip. Thus, for a patient weighing 70 kilograms, the preferred daily dose of the total active ingredients would be about 0.0007 mg/kg/day to about 35 mg/kg/day, and more preferable, 0.007 mg/kg/day to about 15 mg/kg/day. Nonetheless, as will be understood by those of skill in the art, in certain situations it may be necessary to administer the active ingredients disclosed herein in amounts that excess, or even far exceed, the above-stated, preferred dosage range to treat effectively and aggressively a desired condition or characteristic.

In some embodiments, the compositions can be orally or non-orally administered to a human patient in the amount of about 0.0007 mg/day to about 7,000 mg/day of the total active ingredients, and more preferably about 0.07 mg/day to about 70 mg/day of the total active ingredients at, one time per day or in other embodiments, over two to about ten times per day.

Ingredients disclosed herein can be evaluated for efficacy and toxicity using known methods. For example, the toxicology of a particular compound or ingredient, or of a subset of the compounds, sharing certain chemical moieties, may be established by determining in vitro toxicity towards a cell line, such as a mammalian, and preferably a human, cell line. The results of such studies are often predictive of toxicity in animals, such as mammals, or more specifically, humans. Alternatively, the toxicity of particular compounds or ingredients in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including the conditions abated by the compounds or ingredients disclosed herein, including obesity. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound or ingredient in humans The active ingredients described above may be used alone or in combination with one another, or in combination with other therapeutic or diagnostic agents. These products can be utilized in vivo or in vitro. The useful dosages and the most useful modes of administration will vary depending upon the age and weight of the consumer, the particular ingredients employed, and the specific use for which these ingredients are employed.

Synergistic Effects of PE in Combination with Fluconazole

A strain of S. cerevisae was cultured on plates with media with and without PE. As shown, PE enhances the antifungal activity of fluconazole. Filters containing 0 µg, 25 µg, 50 µg, 100 µg fluconazole were placed in the center of the plates. Inhibition of S. cerevisae growth was observed as a clear zone around the filters. The results are shown in FIG. 1. The combination of PE with fluconazole was observed to have a synergistic effect for the inhibition of S. cerevisae growth. PE significantly enhanced the potency of fluconazole to inhibit growth of the S. cerevisae. The larger zone of inhibition on the PE plates surrounding a filter disk with the same concentrations of fluconazole indicates increased fluconazole sensitivity.

The Effects of PE to Increase the Sensitivity of Yeast to Fluconazole

Figure 2:
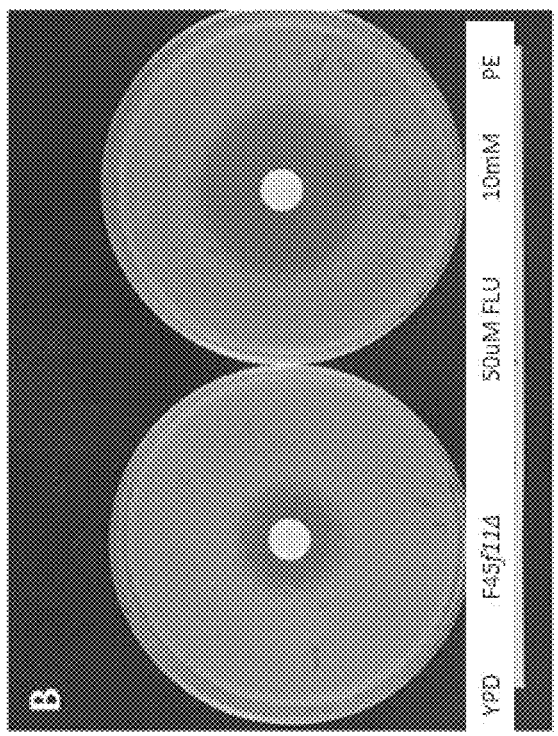
FIG. 2 shows that PE-Fluconazole interaction not explained by its effect on biofilm formation. PE sensitizes *S. cerevisiae* to fluconazole (FLU) in a mutant (flo11Δ) that is unable to form biofilm structures. In each panel, the left plate is YPD alone and the right plate is YPD plus 10 mM PE (a concentration that inhibits biofilm formation)
Figure 2:
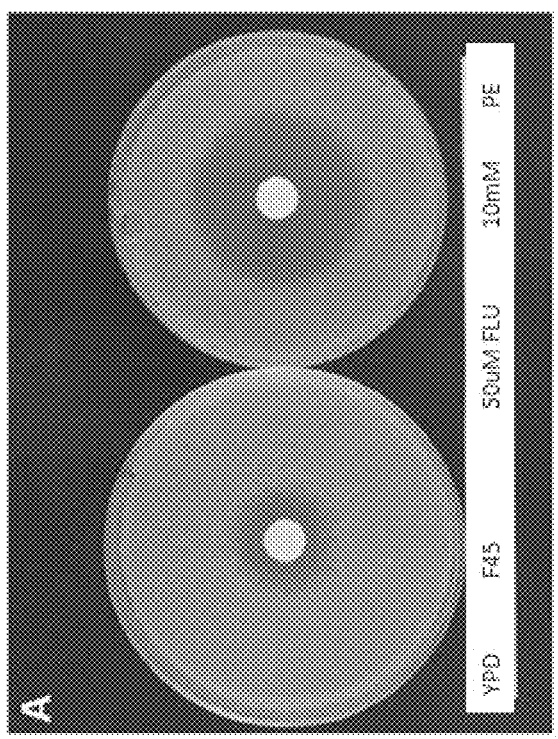

Two different approaches to test whether PE's ability to increase the sensitivity of yeast to fluconazole (i.e. to decrease the concentration of drug needed to inhibit cell growth) could be explained by its ability to disrupt biofilm formation. First a strain that harbors a genetic mutation (flo11D) that prevents biofilm formation (i.e. smooth colonies) was tested for its sensitivity to fluconazole was examined. As PE increased the sensitivity of the flo11D strain as much as it did the wild-type strain (FIG. 2), it was expected that the effect of PE on drug sensitivity is independent of its effect on biofilm formation. The effects of biofilm formation by Candida albicans have been previously described by Zhihao et al, included in its entirety by reference.

As shown in FIG. 1, PE enhances the PE enhances the antifungal activity of fluconazole. Each panel shows 2 YPD (yeast extract peptone dextrose) plates spread with a lawn of S. cerevisiae (F45). In each panel, the left plate is YPD alone and the right plate is YPD plus 10 mM PE (a concentration that inhibits the fluffy colony morphology). Each plate also contains a paper disk that contains a DMSO vehicle, 25 µg fluconazole, 50 µg fluconazole, or 100 µg fluconazole. The larger zone of inhibition on the PE plates surrounding a filter disk with the same concentrations of fluconazole indicates increased fluconazole sensitivity.

Figure 3:
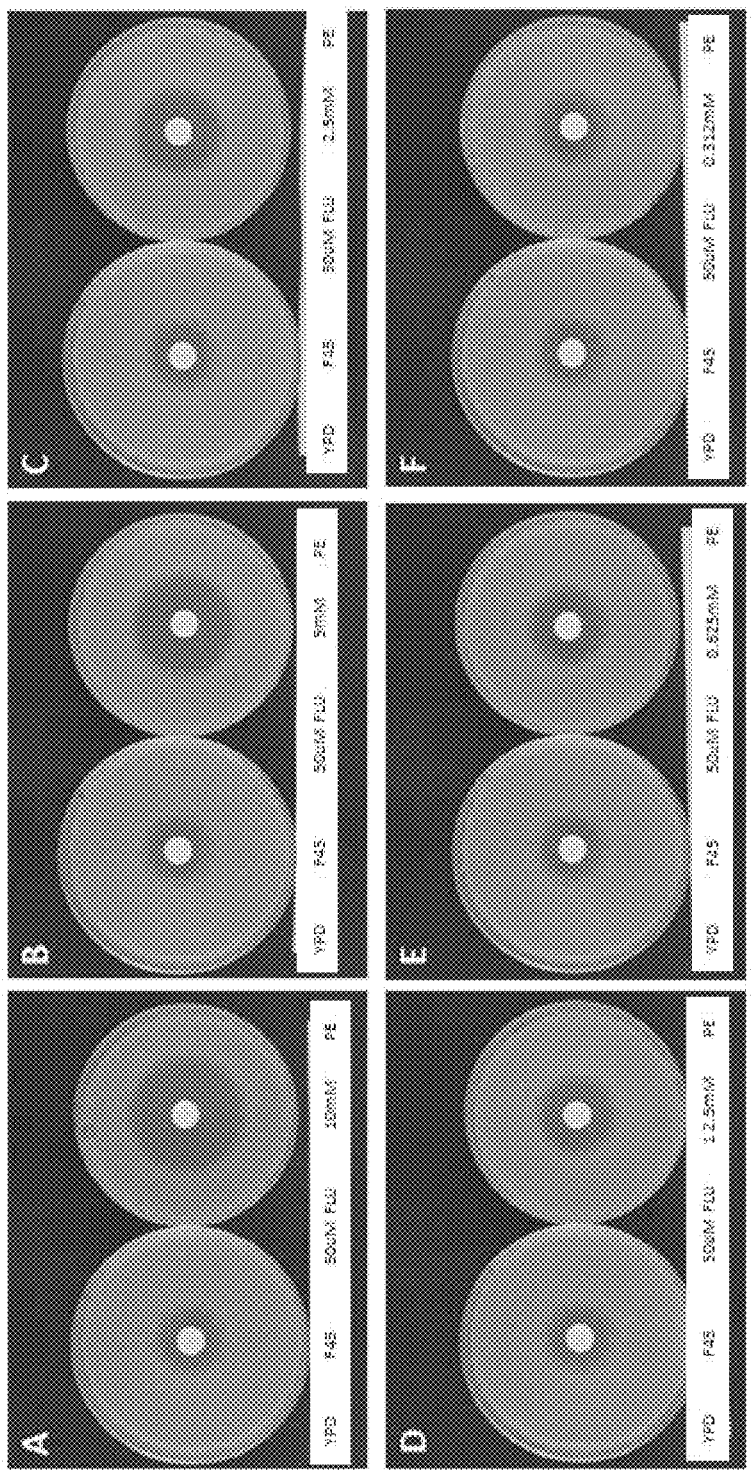
FIG. 3 is a photograph of a series of plate assays showing PE's ability to increase the sensitivity of yeast to fluconazole. As shown, fluconazole was kept at a constant concentration of 50 μM, while the concentrations of PE varied from 10 mM PE to 0.312 mM PE. All plates in all panels are spread with F45 and also contain disks with 50 μg FLU. In each panel, the left plate is YPD alone and the right plate is YPD plus 10 mM PE (FIG. 3, panel A), 5 mM PE (FIG. 3, panel B), 2.5 mM PE (FIG. 3, panel C), 1.25 mM PE (FIG. 3, panel D), 625 μM PE (FIG. 3, panel E), or 312 μM PE (FIG. 3, panel F).

However, previous experiments determined that biofilm formation was inhibited at PE concentrations of 10 mM or higher. Attention is drawn to FIG. 2, in which concentrations of PE that were too low to inhibit biofilm formation (determined by colony morphology) were also shown to increase the sensitivity of the yeast strain flo11D for the fluconazole which further support the hypothesis that the effect of PE on drug sensitivity is independent of its effect on biofilm formation. As such, there is a synergistic effect upon the combination of PE with fluconazole, in which the cells are more sensitive to fluconazole in the presence of PE at a higher concentration (10 mM PE). As shown in FIG. 3, the concentration of fluconazole remained constant at 50 µM, and in combination with PE, the PE was evaluated at concentrations of 10 mM, 5 mM, 2.5 mM, 1.25 mM, 0.625 mM and 0.312 mM.). It is noted that even at lower concentrations of PE (<10 mM), in which the colonies are fluffy, indicating an intact cell wall or intact morphology, the PE at lower concentrations can still enhance killing by fluconazole. Increased sensitivity to FLU (larger growth inhibition zones) are seen with concentrations of PE (625 mM) PE 8-fold below the concentration that disrupts biofilm formation. As such, even at a lower concentration, PE in combination with fluconazole has a synergistic effect on inhibiting the growth of the fungal strain.

PE Increases the Efficacy of Some But Not All Antifungal Drugs

Figure 4:
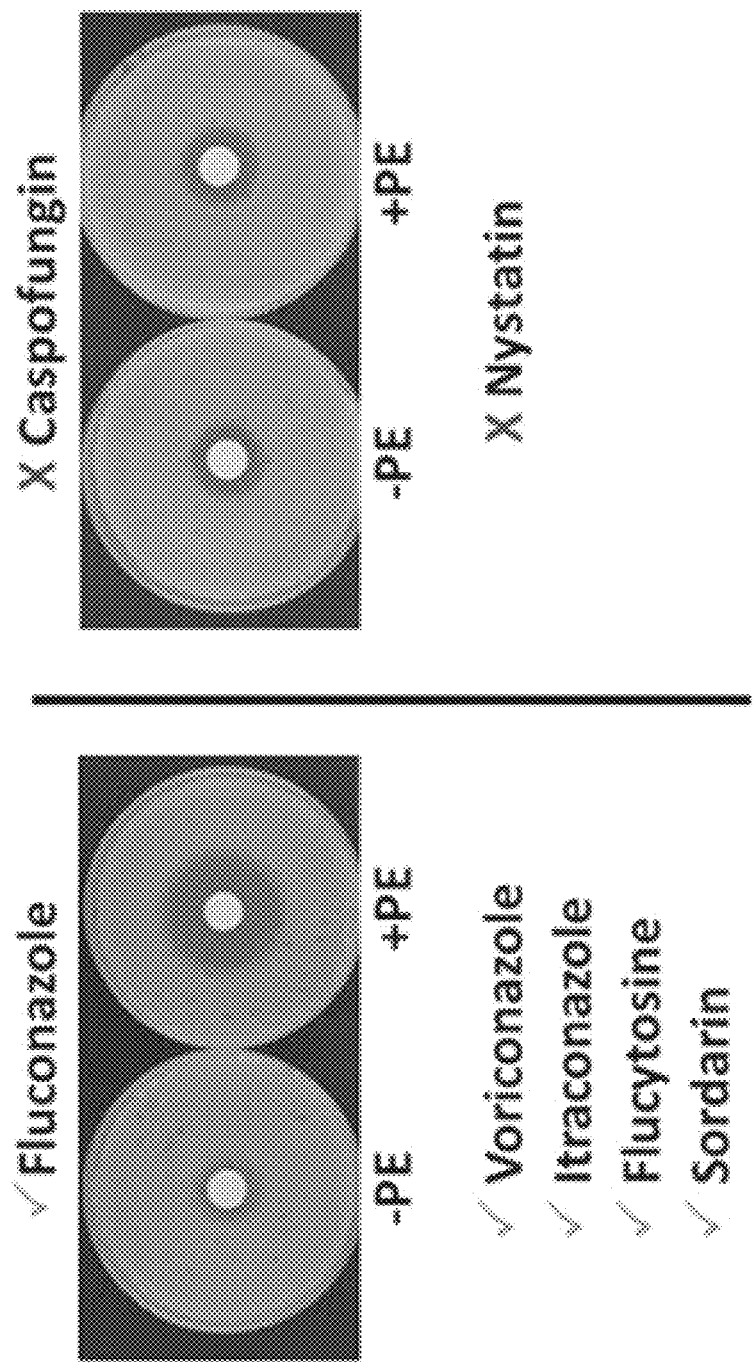
FIG. 4 shows the effects of antifungals in the presence of PE.

As shown in FIG. 4, PE was used in conjunction with several antifungal drugs such as fluconazole, voroconazole, itraconazole, flucytosine, sordarin, caspofungin and nystatin. In several of the embodiments described herein, PE increased the sensitivity of the fungus to fluconazole, voroconazole, itraconazole, flucytosine and sordarin.

PE Enhances the Sensitivity of S. cerevisiae to Voroconazole

Figure 5:
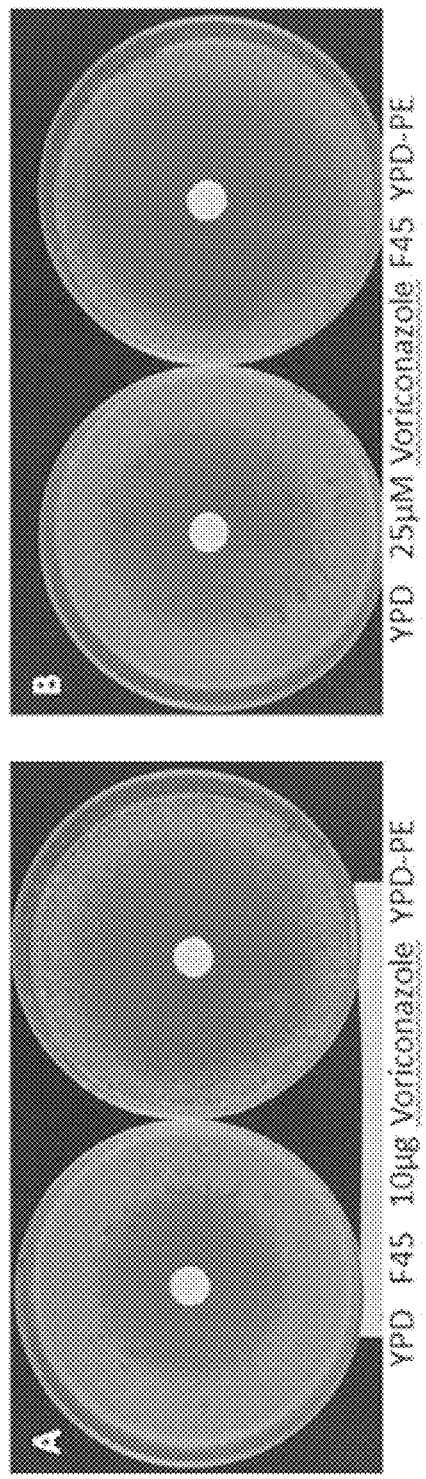
FIG. 5. shows that PE enhances the sensitivity of *S. cerevisiae* to Voriconazole. In each panel, the left plate is YPD alone and the right plate is YPD plus 10 mM PE. Each plate is spread with F45 and also contains a filter disk with 10 μg voriconazole (FIG. 5, panel A) and 25 μg voriconazole (FIG. 5, panel B).

As shown in FIG. 5, PE was used in conjunction with the antifungal, Voriconazole. YPD plates were incubated with S. cerevisiae in which the YPD plates included 10 mM PE. Each plate was spread with F45 strains and also contained a filter disk with 10 mg voriconazole (FIG. 5, panel A) and 25 mg voriconazole (FIG. 5, panel B). As shown, there is an increase in cell clearance in the plates that include the highest concentration of voriconazole.

PE Enhances the Sensitivity of S. cerevisiae to Itraconazole

Figure 6:
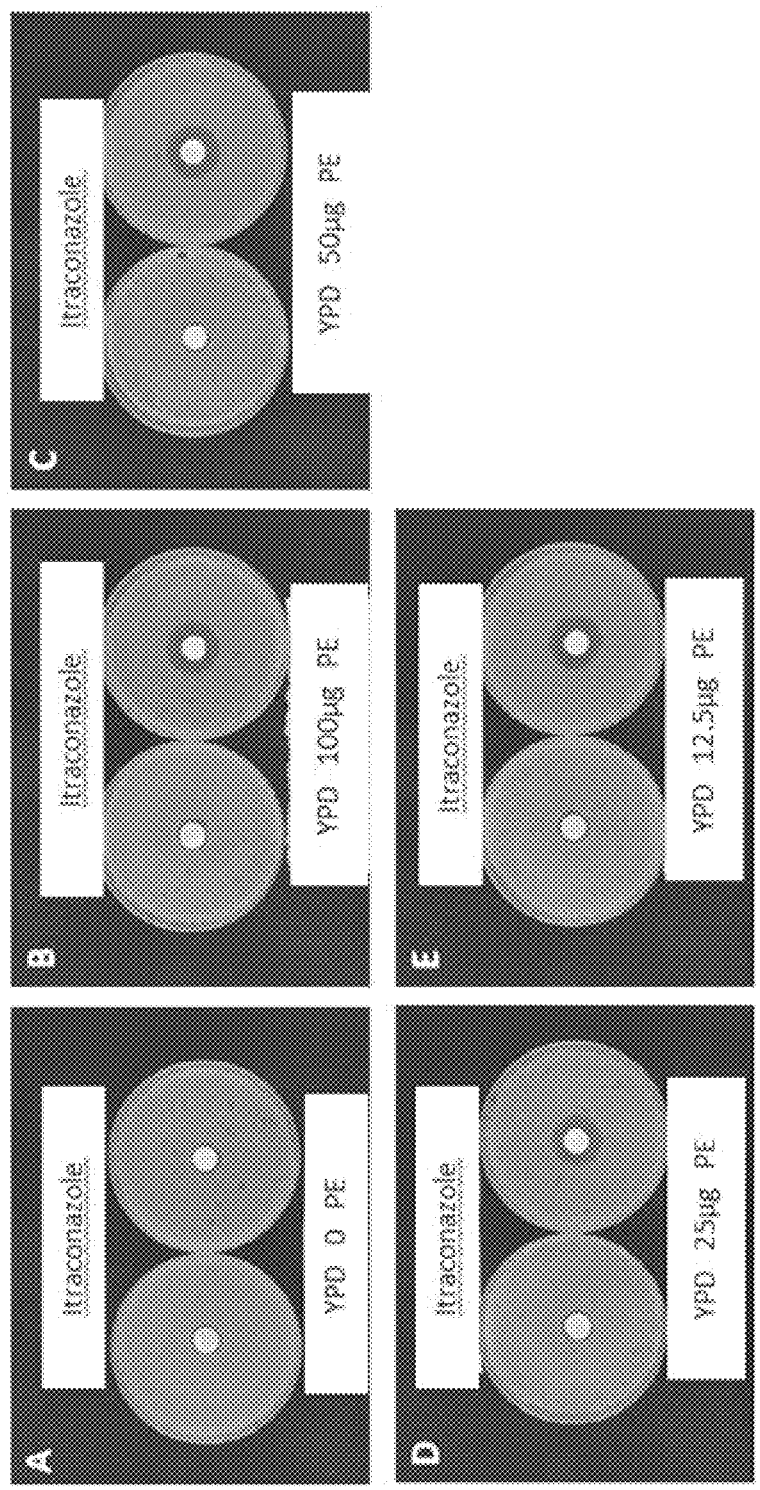
FIG. 6. PE enhances the sensitivity of *S. cerevisiae* to Itraconazole although Itraconazole solubility is a confounding factor. In each panel, the left plate is YPD alone and the right plate is YPD plus 10 mM PE Each plate is spread with F45 and also contains a filter disk with the chloroform vehicle (FIG. 6, panel A), 100 μg Itraconazole (FIG. 6, panel B), 50 μg Itraconazole (FIG. 6, panel C), 25 μg Itraconazole (FIG. 6, panel D), or 12.5 μg Itraconazole (FIG. 6, panel E).

As shown in FIG. 6, PE was used in conjunction with the antifungal, Itraconazole. YPD plates were incubated with S. cerevisiae in which the YPD plates included 10 mM PE. Despite its relative insolubility, as shown in FIG. 6, there as a similar sized zone of inhibition in the presence of different amounts of drug. In each panel, the left plate is YPD alone and the right plate is YPD plus 10 mM PE. YPD plates were incubated with *S. cerevisiae* in which the YPD plates included 10 mM PE. Each plate was spread with F45 strains and also contained a filter disk with the chloroform vehicle (FIG. 6, panel A), 100 mg Itraconazole (FIG. 6, panel B), 50 mg Itraconazole (FIG. 6, panel C), 25 mg Itraconazole (FIG. 6, panel D), or 12.5 mg Itraconazole (FIG. 6, panel E). The presence of a significant difference between +/−PE in the 12.5 mg Itraconazole panel suggests that PE will sensitize yeast to Itraconazole levels below this concentration.

PE Enhances the Sensitivity of *S. cerevisiae* to Sordarin

Figure 7:
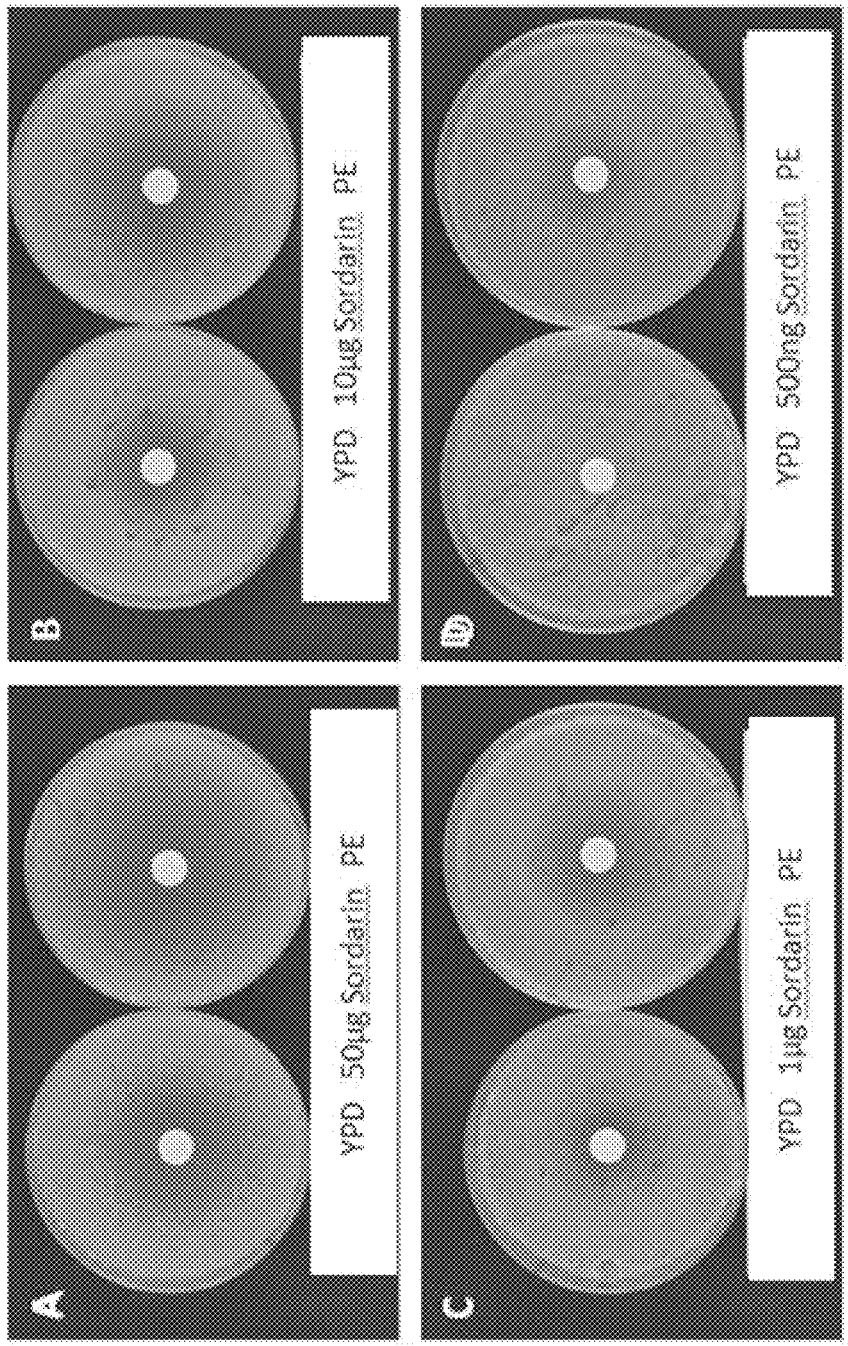
FIG. 7. PE enhances the sensitivity of *S. cerevisiae* to Sordarin. In each panel, the left plate is YPD alone and the right plate is YPD plus 10 mM PE. Each plate is spread with F45 and also contains a filter disk with 50 μg Sordarin (FIG. 7, panel A), 10 μg Sordarin (FIG. 7, panel B), 1 μg Sordarin (FIG. 7, panel C), or 500 ng Sordarin (FIG. 7, panel D).

As shown in FIG. 7, PE was used in conjunction with the antifungal, Sordarin. YPD plates were incubated with *S. cerevisiae* in which the YPD plates included 10 mM PE. Each plate was spread with F45 and also contained a filter disk with 50 mg Sordarin (FIG. 7, panel A), 10 mg Sordarin (FIG. 7, panel B), 1 mg Sordarin (FIG. 7, panel C), or 500 ng Sordarin (FIG. 7, panel D). As shown, PE sensitizes *S. cerevisiae* to Sordarin, a pre-clinical selective inhibitor of fungal protein synthesis that impairs translational elongation factor 2 (EF-2) function.

PE Has No Effect on the Caspofungin Sensitivity of *S. cerevisiae*

Figure 8:
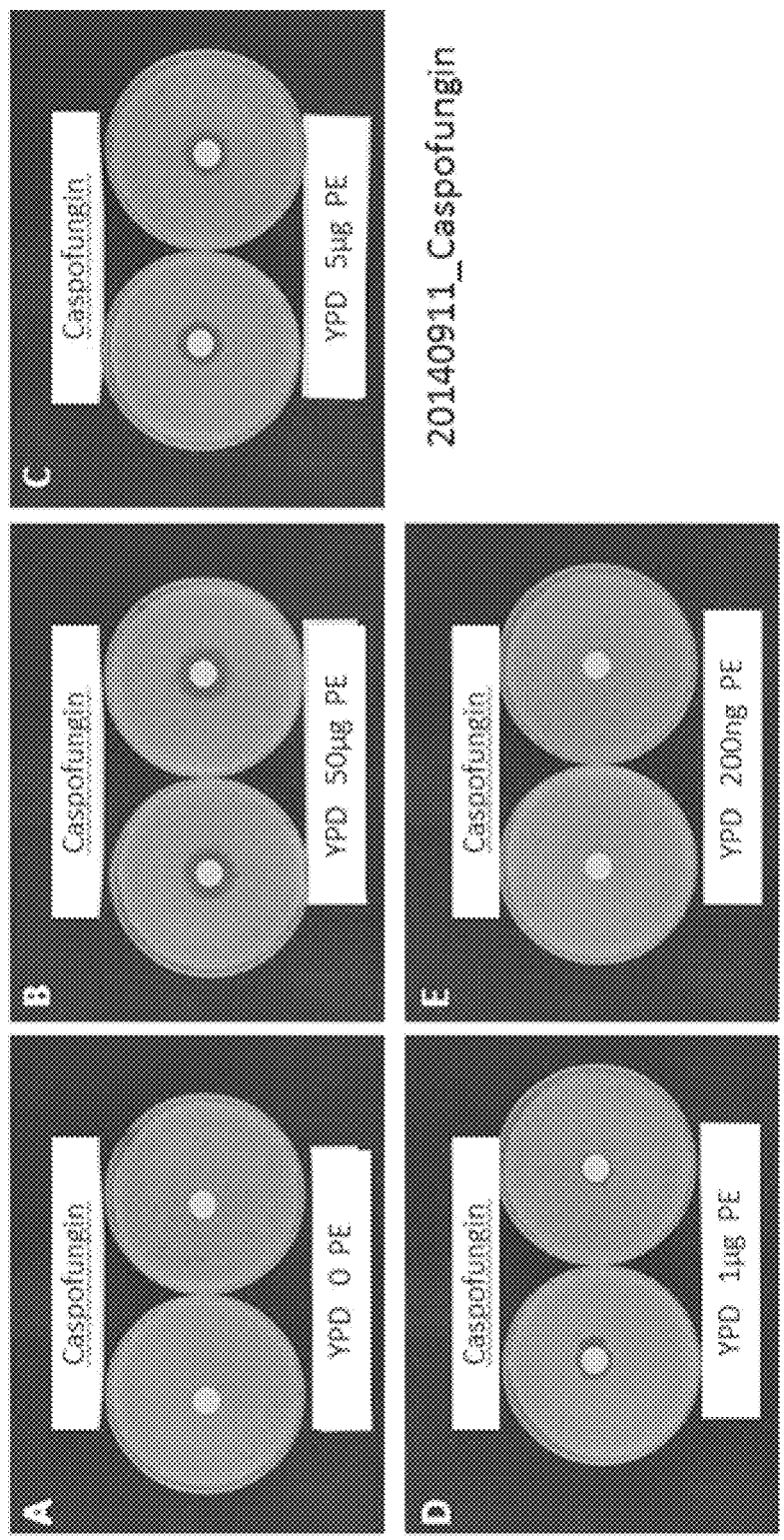
FIG. 8 shows that PE has no effect on the sensitivity of *S. cerevisiae* to Caspofungin, an echinocandin that targets the fungal cell wall by inhibiting b-glycan synthase. In each panel, the left plate is YPD alone and the right plate is YPD plus 10 mM PE. Each plate is spread with F45 and also contains a filter disk with the water vehicle (FIG. 8, panel A), 50 µg Caspofungin (FIG. 8, panel B), 5 µg Caspofungin (FIG. 8, panel C), 1 µg Caspofungin (FIG. 8, panel D), or 200 ng Caspofungin (FIG. 8, panel E).

As shown in FIG. 8, PE was used in conjunction with the antifungal, Caspofungin, an echinocandin that targets the fungal cell wall by inhibiting b-glycan synthase. YPD plates were incubated with *S. cerevisiae* in which the YPD plates included 10 mM PE. In each panel, the left plate is YPD alone and the right plate is YPD plus 10 mM PE. Each plate was spread with F45 and also contained a filter disk with the water vehicle (FIG. 8, panel A), 50 µg Caspofungin (FIG. 8, panel B), 5 µg Caspofungin (FIG. 8, panel C), 1 µg Caspofungin (FIG. 8, panel D), or 200 ng Caspofungin (FIG. 8, panel E). There is no significant difference between the zone sizes PE Has No Effect on the Nystatin Sensitivity of *S. cerevisiae*

Figure 9:
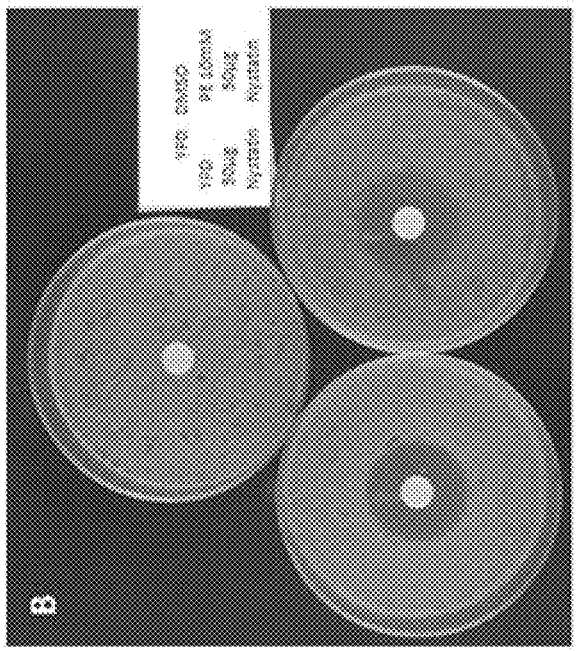
FIG. 9 shows that PE does not increase the sensitivity to Nystatin, a polyene that binds ergosterol thereby weakening the plasma membrane. In each panel, the top plate is YPD alone with a disc that contains DMSO, the bottom left plate is YPD alone with a disc that contains 50 µg Nystatin and the bottom right plate is YPD plus 10 mM PE with a disc that contains 50 µg Nystatin. The plates in FIG. 9, panel A are spread with the F45 strain. The plates in FIG. 9, panel B are spread with the BY4741 lab strain.
Figure 9:
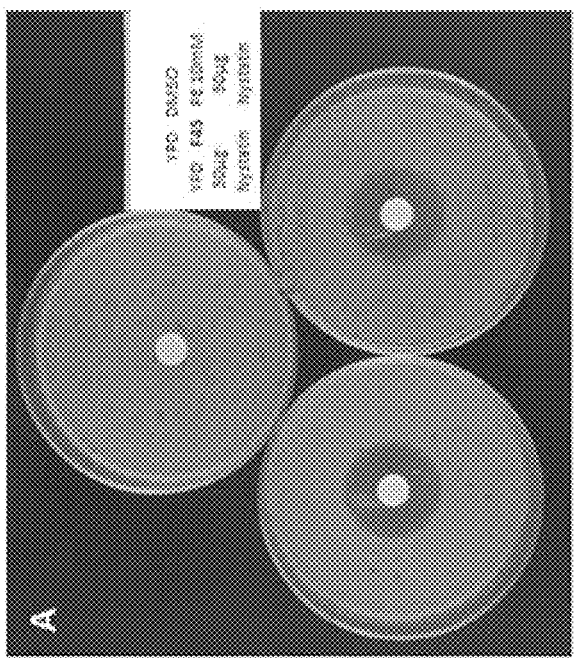

As shown in FIG. 9, PE was used in conjunction with the antifungal, Nystatin, a polyene that binds ergosterol thereby weakening the plasma membrane. In each panel, the top plate is YPD alone with a disc that contains DMSO, the bottom left plate is YPD alone with a disc that contains 50 µg Nystatin and the bottom right plate is YPD plus 10 mM PE with a disc that contains 50 µg Nystatin. The plates in panel are spread with the F45 strain (FIG. 9, panel A). The plates in FIG. 9, panel B are spread with the BY4741 lab strain. There is no significant difference between the zone sizes+/−PE. As shown, there was no significant difference between the zone sizes+/−PE.

PE Increases the Efficacy of Specific Antifungal Drugs in Pathogenic Fungi

PE was also shown to increase the efficacy of specific antifungal drugs in pathogenic fungi (Table 1). Furthermore, in several of the described embodiments, and as also shown in Table 1, experimentation have shown that that PE is able to increase the efficacy of the triazoles against a wide range of opportunistic fungal pathogens. In two cases, a fluconazole resistant strain of *C. albicans* and a fluconazole resistant strain of *Apergillus fumigatus*, the PE-triazole effect was synergistic, and there was a correlation between drug resistance and synergy with PE.

TABLE 1

| Species | Fluconazole (µg) | | Voriconazole (µg) | |
|---|---|---|---|---|
| | MIC | FICI | MIC | FICI |
| Candida albicans (resistant) | >128 | 0.6 | >128 | 0.3 |
| Aspergillus fumigatus | >128 | 0.5 | 0.25 | 0.6 |
| Candida tropicalis | >128 | 1.0 | 32 | 0.6 |
| Candida krusei | 32 | 1.1 | 0.25 | 1.1 |
| Candida glabrata | 8 | 1.4 | 0.5 | 1.2 |
| Candida albicans (sensitive) | 1 | 1.5 | 0.03125 | 2.1 |
| Candida parapsilosis | 1 | 1.6 | 0.03125 | 1.6 |
| Cryptococcus neoformans | 0.25 | 1.1 | 0.0156 | 1.1 |

Method: the effects of PE on the efficacy of fluconazole and voriconazole were tested against 2 strains of *C. albicans* (sensitive=ATCC 90028 and resistant=20186.025; 8357) and one strain each of *Candida glabrata* (ATCC 36583), *Candida krusei* (ATCC 6258), *Candida parapsilosis* (ATCC 22019), *Candia tropicalis* (ATCC 200956), *Cryptococcus neoformans* (ATCC 24067), and *Aspergillus fumigatus* (ATCC 13073). The of PE, fluconazole, and voriconazole for each strain were determined. Checkboard assays to determine the FICI values were performed. Values were close to or below the FICI value that is widely accepted as a synergistic interaction (FICI=0.5).

Figure 10:
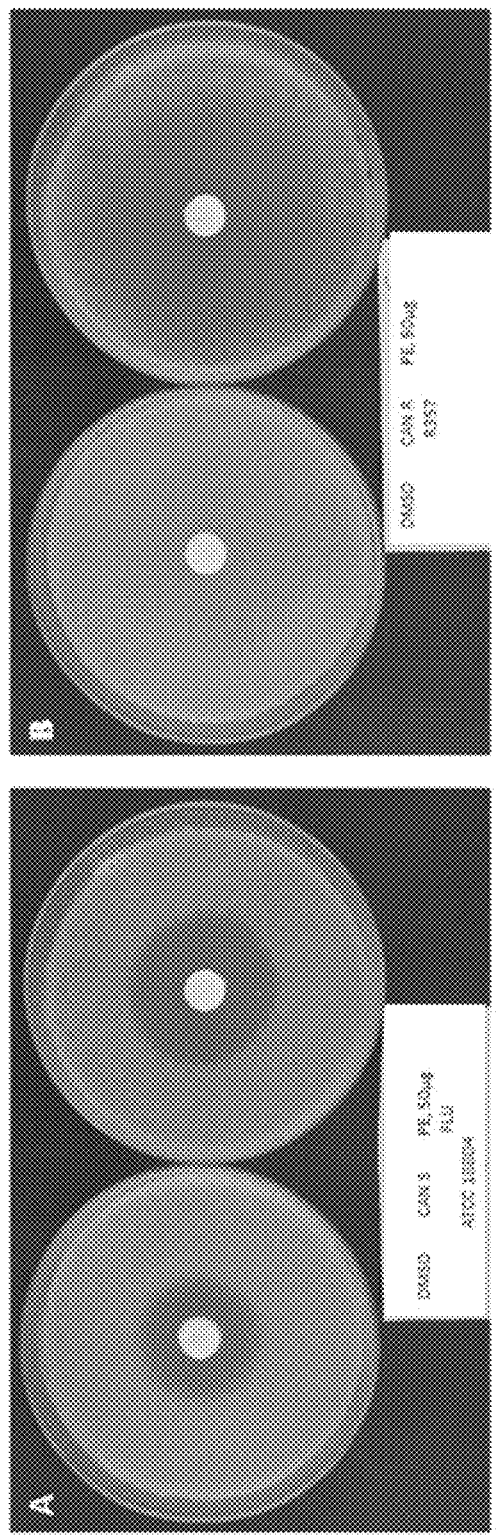
FIG. 10 shows that PE increases the efficacy of fluconazole against C. albicans. In each panel, the left plate is YPD plus 1% DMSO and the right plate is YPD plus 10 mM PE in 1% DMSO. Each panel plate also contains a filter disk with 50 µg fluconazole. The plates in FIG. 10, panel A are spread with a fluconazole sensitive strain of C. albicans (ATCC 18804). The plates in FIG. 10, panel B are spread with the same fluconazole resistant strain of C. albicans used in the Eurofins checkerboard assay (R357).
Figure 14:
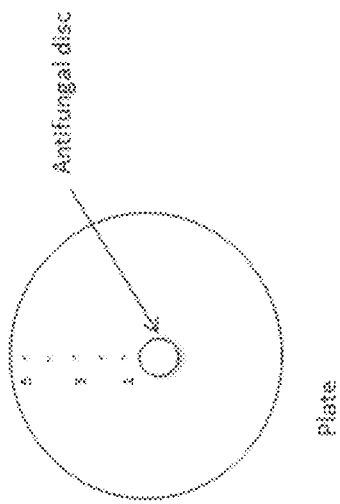
FIG. 14 shows a schematic of the degrees of clearance in a plate spread with fungal cells.

PE Can Re-Sensitize Drug Resistant Strains of *C. albicans* to Fluconazole with an Effect That is Even Stronger Than the Effect on Drug Sensitive Strains In the following embodiments, it was shown that PE can re-sensitize drug resistant strains of *C. albicans* to fluconazole with an effect that is even stronger than the effect on drug sensitive strains (FIGS. 10 and 11), A similar result was also seen with flucytosine (FIG. 9). However, the effects with sordarin appear to be additive, at least for the one strain of *C. albicans* tested (FIG. 10). A summary of the effects of PE in conjunction with several types of antifungals is shown in Tables 2A-J which show the degrees of clearance as described in FIG. 14.

TABLE 2A

| | Voriconazole sensitivity | | | |
|---|---|---|---|---|
| | FIG. 5 | | | |
| | Panel A | | Panel B | |
| Plate | YPD + 10 µg voriconazole | YPD + 10M PE 10 µg voriconazole | YPD + 25 µg voriconazole | YPD + 10M PE 25 µg voriconazole |
| Degree of clearance | 3 | 5 | 4 | 5 |

TABLE 2B

Itraconazole sensitivity

FIG. 6

| Plate | Panel A | | Panel B | | Panel C | | Panel D | | Panel E | |
|---|---|---|---|---|---|---|---|---|---|---|
| | YPD | YPD + 10 mM PE | YPD | YPD + 10 mM PE + 100 µg Itraconazole | YPD | YPD + 10 mM PE + 50 µg Itraconazole | YPD | YPD + 10 mM PE + 25 µg Itraconazole | YPD | YPD + 10 mM PE + 12.5 µg Itraconazole |
| Degree of clearance | 0 | 0 | 0 | 1 | 0 | 1 | 0 | 1 | 0 | 1 |

TABLE 2C

Sordarin sensitivity

FIG. 7

| Plate | Panel A | | Panel B | | Panel C | | Panel D | |
|---|---|---|---|---|---|---|---|---|
| | YPD | YPD + 10 mM PE + 50 µg Sordarin | YPD | YPD + 10 mM PE + 10 µg Sordarin | YPD | YPD + 10 mM PE + 1 µg Sordarin | YPD | YPD + 10 mM PE + 500 ng Sordarin |
| Degree of clearance | 8 | 4 | 2 | 3 | 2 | 0 | 1 | |

TABLE 2D

Caspofungin sensitivity

FIG. 8

| Plate | Panel A | | Panel B | | Panel C | | Panel D | | Panel E | |
|---|---|---|---|---|---|---|---|---|---|---|
| | YPD | YPD + 10 mM PE 50 µg Caspofungin | YPD | YPD + 10 mM PE + 50 µg Caspofungin | YPD | YPD + 10 mM PE + 5 µg Caspofungin | YPD | YPD + 10 mM PE + 1 µg Caspofungin | YPD | YPD + 10 mM PE + 200 ng Caspofungin |
| Degree of clearance | 0 | 0 | 1 | 1 | 1 | 1 | 1 | 0 | 0 | 0 |

TABLE 2E

Nystatin sensitivity

FIG. 9

| Strain/Plate | Panel A Strain F45 | | | Panel B Strain BY4741 | | |
|---|---|---|---|---|---|---|
| | YPD/DMSO | YPD + 50 µg nystatin | YPD + 10 mM PE + 50 µg nystatin | YPD/DMSO | YPD + 50 µg nystatin | YPD + 10 mM PE + 50 µg nystatin |
| Degree of clearance | 0 | 2 | 2 | 0 | 2 | 2 |

TABLE 2F

Fluconazole sensitivity

FIG. 10

| | Panel A<br>Strain ATCC 18804 | | Panel B<br>Strain ATCC 18804 from R357 assay | |
| --- | --- | --- | --- | --- |
| Strain/<br>Plate | YPD/DMSO + 50 μg<br>fluconazole | YPD + 10 mM PE + 50 μg<br>fluconazole | YPD/DMSO + 50 μg<br>fluconazole | YPD + 10 mM PE + 50 μg<br>fluconazole |
| Degree of<br>clearance | 1 | 2 | 0 | 5 |

TABLE 2G

Fluconazole strains sensitivity

FIG. 11

| | Panel A<br>Strain F45 | | Panel B<br>Strain C albicans 304 | | Panel C<br>Strain CATW 4/19 | |
| --- | --- | --- | --- | --- | --- | --- |
| Strain/<br>Plate | YPD + 50 μg<br>Fluconazole | YPD + 10 mM PE +<br>50 μg Fluconazole | YPD + 50 μg<br>Fluconazole | YPD + 10 mM PE +<br>50 μg Fluconazole | YPD + 50 μg<br>Fluconazole | YPD + 10 mM PE +<br>50 μg Fluconazole |
| Degree of<br>clearance | 1 | 3 | 3 | 5 | 2 | 4 |

TABLE 2H

Fluconazole strains sensitivity

FIG. 11

| | Panel D<br>Strain C albicans 3147 | | Panel E<br>Strain C albicans 20136.025 | |
| --- | --- | --- | --- | --- |
| Strain/<br>Plate | YPD + 50 μg<br>Fluconazole | YPD + 10 mM PE + 50 μg<br>Fluconazole | YPD + 50 μg<br>Fluconazole | YPD + 10 mM PE + 50 μg<br>Fluconazole |
| Degree of<br>clearance | 0 | 3 | 0 | 5 |

TABLE 2I

Efficacy of Flucytosine with PE

FIG. 12

| | Panel A<br>Strain C albicans 18804 | | Panel B<br>Strain R357 | |
| --- | --- | --- | --- | --- |
| Strain/<br>Plate | YPD + DMSO + 100 μg<br>Fluconazole | YPD + 10 mM PE + 100 μg<br>Fluconazole | YPD + DMSO + 100 μg<br>Fluconazole | YPD + 10 mM PE + 100 μg<br>Fluconazole |
| Degree of<br>clearance | 3 | 5 | 2 | 5 |

TABLE 2J

Efficacy with sordarin

FIG. 13

| | Panel A | | Panel B | | Panel C | |
|---|---|---|---|---|---|---|
| Plate | YPD + 1 µg sordarin | YPD + 1 µg sordarin + 10 mM PE | YPD + 10 µg sordarin | YPD + 10 µg sordarin + 10 mM PE | YPD + 50 µg sordarin | YPD + 50 µg sordarin + 10 mM PE |
| Degree of clearance | 1 | 2 | 2 | 3 | 3 | 4 |

PE Increases the Efficacy of Fluconazole Against *C. albicans*

PE was used in conjunction with the antifungal, floconazole as shown in FIG. 10, and was shown to increase the antifungals efficacy. In each panel, the left plate is YPD plus 1% DMSO and the right plate is YPD plus 10 mM PE in 1% DMSO. Each panel plate also contains a filter disk with 50 mg fluconazole. The plates in FIG. 10, panel A are spread with a fluconazole sensitive strain of *C. albicans* (ATCC 18804). The plates in FIG. 10, panel B are spread with the same fluconazole resistant strain of *C. albicans* used in the Eurofins checkerboard assay (R357). While the zones of both strains are larger in the presence of PE, the zone of the resistant strain is substantially larger than the zone of the sensitive strain. These results with a different assay and a different drug sensitive strain of *C. albicans* supports the result of the C.R.O., that the PE-fluconazole combination is even more effective against this flu-resistant strain (R357).

Figure 11:
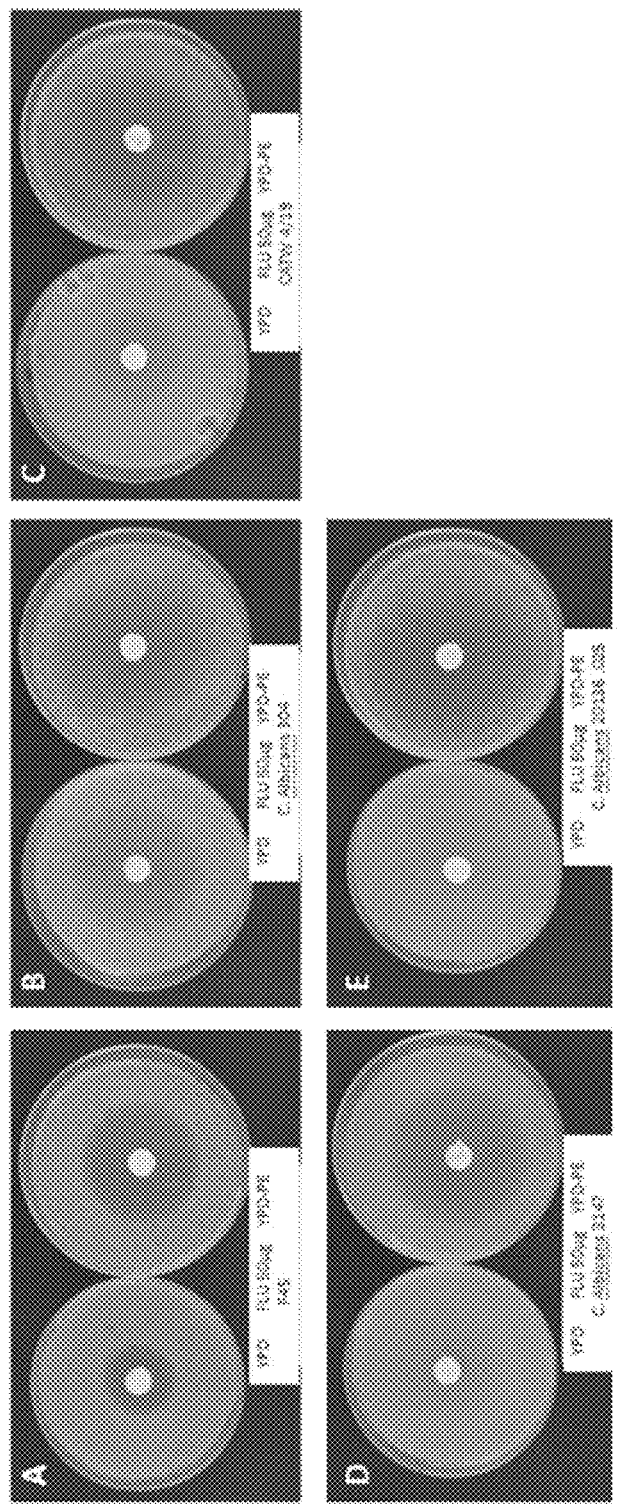
FIG. 11 shows that PE increases the efficacy of fluconazole against several resistant C. albicans strains. In each panel, the left plate is YPD and the right plate is YPD plus 10 mM PE. Each panel plate also contains a filter disk with 50 µg fluconazole. The plates are spread with the S. cerevisiae strain F45 (FIG. 11, panel A) or one of four fluconazole resistant strains of C. albicans (304 (ATCC 28121) FIG. 11, panel B), (CATW 4/19 (ATCC 90819) FIG. 11, panel C), 3147 (ATCC 10231) (FIG. 11, panel D), and 8357 (FIG. 11, panel E).

PE Increases the Efficacy of Fluconazole Against Several Resistant *C. albicans* Strains PE was used in conjunction with the antifungal, floconazole as shown in FIG. 11, and was shown to increase the antifungals efficacy against several strains of *C. albicans*, such as *S. cerevisiae* strain F45 and four fluconazole resistant strains of *C. albicans* (304(ATCC 28121), CATW 4/19 (ATCC 90819), 3147 (ATCC 10231 and R357). In each panel, the left plate is YPD and the right plate is YPD plus 10 mM PE. Each panel plate also contains a filter disk with 50 mg fluconazole. The plates were spread with the *S. cerevisiae* strain F45 or one of four fluconazole resistant strains of *C. albicans* (FIG. 11, panel A), 304 (ATCC 28121) (FIG. 11, panel B), CATW 4/19 (ATCC 90819) (FIG. 11, panel C), 3147 (ATCC 10231) (FIG. 11, panel D), and R357 (FIG. 11, panel E). All resistant *C. albicans* strains show large zones of inhibition in the presence of PE and fluconazole, despite being resistant to fluconazole alone. As such, it was concluded that several drug resistant *C. albicans* strains are highly sensitive to the PE-fluconazole combination.

PE Increases the Efficacy of Flucytosine Against *C. albicans*

Figure 12:
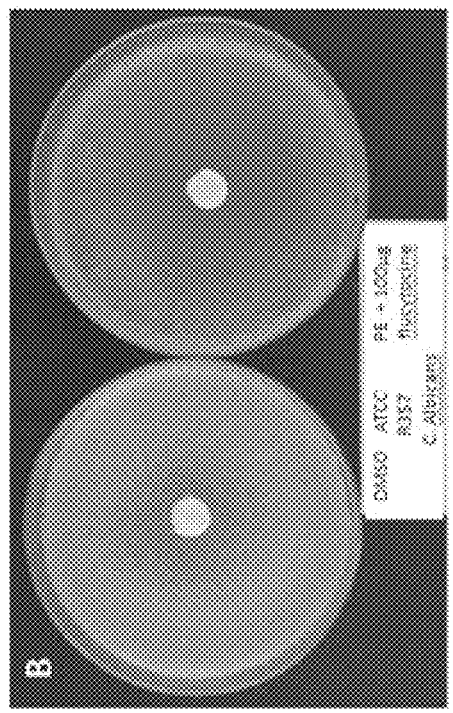
FIG. 12 shows that PE increases the efficacy of flucytosine against C. albicans. In each panel, the left plate is YPD plus 1% DMSO and the right plate is YPD plus 10 mM PE in 1% DMSO. Each panel plate also contains a filter disk with 100 µg flucytosine. The plates in panel are spread with C. albicans strain ATCC #18804 (FIG. 12, panel A). The plates in FIG. 12, panel B are spread with the 8357 strain of C. albicans used in the Eurofins checkerboard assay. Although the boundaries of the flucytosine zones are more diffuse than for some of the other drugs, the zones are larger in the presence of PE and the results look similar to the results with fluconazole (FIG. 10) in that there is a stronger effect on the more resistant strain (FIG. 10, panel B).
Figure 12:
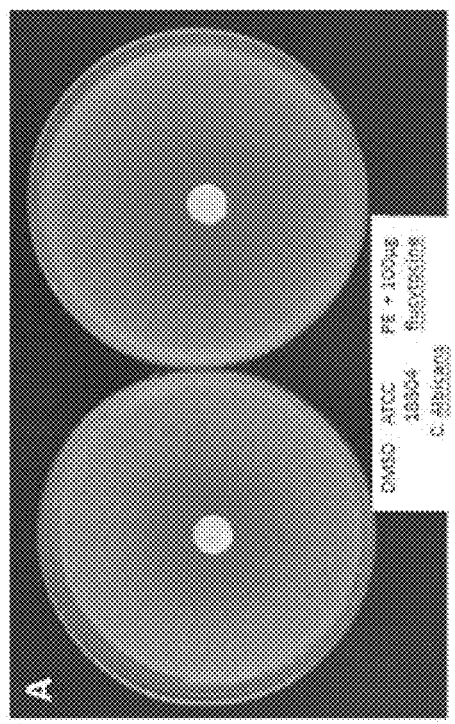

PE was used in conjunction with the antifungal, flucytosine as shown in FIG. 12. In each panel, the left plate is YPD plus 1% DMSO and the right plate is YPD plus 10 mM PE in 1% DMSO. Each panel plate also contains a filter disk with 100 mg flucytosine. The plates in FIG. 12, panel A are spread with *C. albicans* strain ATCC #18804. The plates in FIG. 12, panel B are spread with the R357 strain of *C. albicans* used in the Eurofins checkerboard assay. Although the boundaries of the flucytosine zones are more diffuse than for some of the other drugs, the zones are larger in the presence of PE and the results look similar to the results with fluconazole (FIG. 10) in that there is a stronger effect on the more resistant strain (panel B).

PE-Sordarin Effect Against *C. albicans* 8357 Appears Additive

Figure 13:
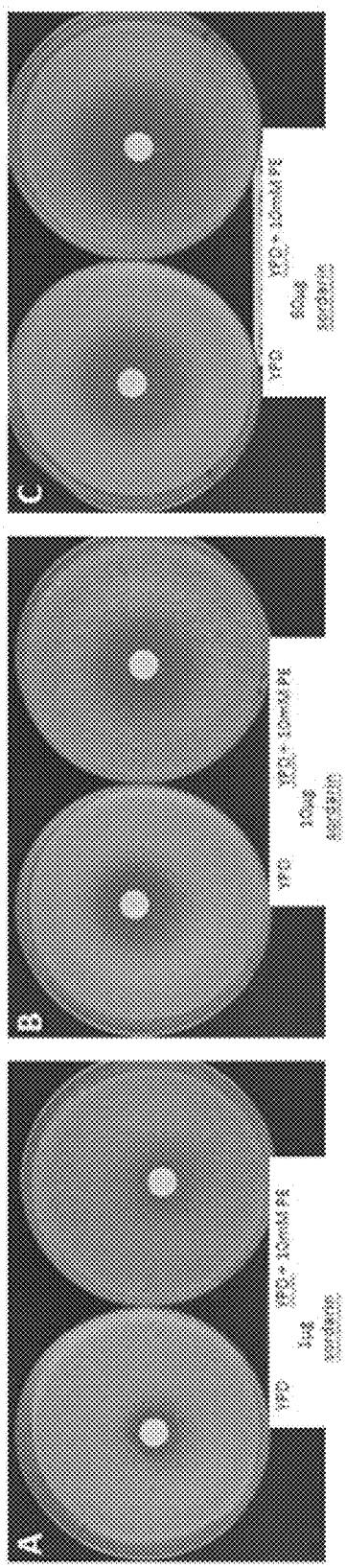
FIG. 13 shows that the PE-sordarin effect against C. albicans R357 appears additive. PE is not synergistic against the 8357 strain in combination with all antifungal drugs. In each panel, the left plate is YPD alone and the right plate is YPD plus 10 mM PE. All plates are spread with the C. albicans strain 8357. Each plate also contains a filter disk with 1 µg sordarin (FIG. 13, panel A), 10 µg sordarin (FIG. 13, panel B), or 50 µg sordarin (FIG. 13, panel C). Although the zone sizes are larger in the presence of PE, the magnitude of the difference appears to be in the additive range.

As shown in FIG. 13, PE is not synergistic against the 8357 strain in combination with all antifungal drugs. In each panel, the left plate is YPD alone and the right plate is YPD plus 10 mM PE. All plates are spread with the *C. albicans* strain 8357. Each plate also contained a filter disk with 1 µg sordarin (FIG. 13, panel A), 10 µg sordarin (FIG. 13, panel B), or 50 µg sordarin (FIG. 13, panel C). Although the zone sizes are larger in the presence of PE, the magnitude of the difference appears to be in the additive range.

Zones of Growth Inhibition Were Measured for the *S. cerevisiae* Strain F45 on YPD Plates Containing 10 mM of the Enamine Compound with a 50 µg Fluconazole Disk Applied Zones of growth inhibition were also measured for strain F45 in which F45 strains were spread on YPD plates that contained 10 mM of an Enamine compound. which was poured into the plate, with a 50 µg fluconazole disk. Enamine is an unsaturated compound derived by the condensation of an aldehyde or ketone with a secondary amine Some enamines have structures that are similar to PE, as such, they were tested to measure their efficacy in increasing sensitivity to an antifungal. As shown in Table 3, are the results of inhibiting the growth of the fungus in the presence of fluconazole and several listed Enamine compounds.

TABLE 3

| Enamine Compound | Compound | Chemical Name | Fluconazole Zone Size, mm* |
|---|---|---|---|
| PEA Control | | $C_8H_{10}O$ | 27 |
| DMSO Vehicle Control | | | 15 |
| 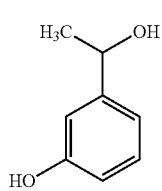 | A | $C_8H_{10}O_2$ | 11 |

TABLE 3-continued
| Enamine Compound | Compound | Chemical Name | Fluconazole Zone Size, mm* |
|---|---|---|---|
| 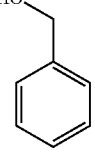 | B | $C_7H_8O$ | 11 |
| 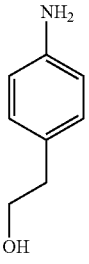 | C | $C_8H_{11}NO$ | 13 |
| 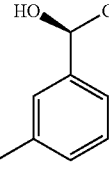 | D | $C_9H_9NO$ | 17 |
| 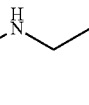 | E | $C_{10}H_{15}NO$ | 35 |
| 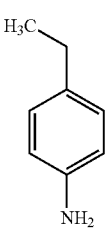 | F | $C_8H_{11}N$ | inhibition by compound but not fluconazole |
| 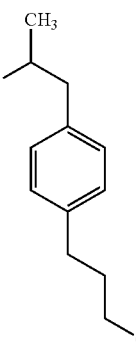 | G | $C_{13}H_{20}O$ | inhibition by compound but not fluconazole |
| 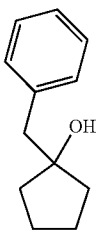 [SMILES: OC1(Cc2ccccc2)CCCC1] | H | $C_{12}H_{16}O$ | no growth |

TABLE 3-continued

| Enamine Compound | Chemical Compound | Chemical Name | Fluconazole Zone Size, mm* |
|---|---|---|---|
| H₂N~~~O~~~phenyl | I | $C_{12}H_{19}NO$ | no growth |
| HO-CH₂CH₂-(3-Cl-phenyl) | J | $C_8H_9ClO$ | no growth |

*Average of three plates

As shown in the control, PE with fluconazole had a high clearance of fungal cells on the plate. However, enamine compounds E, I and J also exhibit loss of growth. In some embodiments herein, enamine compounds can increase the sensitivity of a fungal cell to an antifungal agent. In some embodiments, the enamine compounds are H, or J. The results demonstrate that there is a range of effects, with some compounds having no effect or effects less than that of PE and at least one molecule (E) with activity greater than PE. Because all of these molecules have similar chemical properties, especially with respect to non-specific effects on the plasma membrane, the range of activities supports the hypothesis that the synergistic effects that we see between PE and the triazole class of antifungal drugs has a molecular mechanism that is more specific than, for example increasing membrane permeability.

In some embodiments, a method of increasing the sensitivity of a fungal cell to an antifungal agent is provided. The method can comprise contacting the cell with an enamine compound in combination with the antifungal agent. In some embodiments, the sensitivity of the cell is increased at least about 2-fold compared to a cell not contacted with enamine compound. In some embodiments, the sensitivity of the cell is increased at least about 5-fold compared to a cell not contacted with enamine compound. In some embodiments, the sensitivity of the cell is increased at least about 20-fold compared to a cell not contacted with enamine compound. In some embodiments, the cell is selected from the group consisting of *Candida* spp, *Epidermophyton* spp, *Histoplasma* spp, *Trichophyton* spp, *Microsporum* spp, *Blastomyces* spp, *Histoplasma* spp, *Cryptococcus* spp, *Coccidioides* spp *Pneumocystis* spp, *Saccharomyces* spp, *Aspergillus* spp, *Kluyveromyces* spp, *Schizosaccharomyces* spp, and *Streptomyces* spp. In some embodiments, the *Candida* spp is selected from the group consisting of *C. albicans, C. glabrata, C. rugosa, C. parapsilosis, C. tropicalis*, and *C. dubliniensis*. In some embodiments, the *Epidermophyton* spp is *E. floccosum*. In some embodiments, the antifungal agent is selected from the group consisting of a polyene, an imidazole, a triazole, a thiazole, an allylamine, Sordarin, Flucytosine and an echinocandin. In some embodiments, the polyene is selected from the group consisting of Amphotericin B, Candicidin, Filipin, Hamycin, Natamycin and Rimocidin. In some embodiments, the imidazole is selected from the group consisting of Bifonazole, Butoconazole, Clotrimazole, Econazole, Fenticonazole, Isoconazole, Ketoconazole, Luliconazole, Miconazole, Omoconazole, Oxiconazol, Sertaconazole, Sulconazole, and Tioconazole. In some embodiments, the triazole is selected from the group consisting of Albaconazole, Fluconazole, Isavuconazole, Itraconazole, Posaconazole, Ravuconazole, Terconazole, and Voriconazole. In some embodiments, the thiazole comprises Abafungin. In some embodiments, the allylamine is selected from the group consisting of Amorolfin, Butenafine, Naftifine, and Terbinafine. In some embodiments, the echinocandin is selected from the group consisting of Anidulafungin and Micafungin.

Methods of Increasing the Sensitivity of Fungal Cells to Antifungal Agents

In some embodiments, a method of increasing the sensitivity of a fungal cell to an antifungal agent is provided. The method can comprise contacting the cell with phenyl ethanol in combination with the antifungal agent. In some embodiments, the antifungal agent is selected from the group consisting of a polyene, an imidazole, a triazole, a thiazole, an allylamine, and an echinocandin. In some embodiments, the polyene is selected from the group consisting of Amphotericin B, Candicidin, Filipin, Hamycin, Natamycin, Nystatin, Flucytosine, Sordarin and Rimocidin. In some embodiments, the imidazole is selected from the group consisting of Bifonazole, Butoconazole, Clotrimazole, Econazole, Fenticonazole, Isoconazole, Ketoconazole, Luliconazole, Miconazole, Omoconazole, Oxiconazol, Sertaconazole, Sulconazole, and Tioconazole. In some embodiments, the triazole is selected from the group consisting of Albaconazole, Fluconazole, Isavuconazole, Itraconazole, Posaconazole, Ravuconazole, Terconazole, and Voriconazole. In some embodiments, the thiazole comprises Abafungin. In some embodiments, the allylamine is selected from the group consisting of Amorolfin, Butenafine, Naftifine, and Terbinafine. In some embodiments, the echinocandin is selected from the group consisting of Anidulafungin, Caspofungin, and Micafungin. In some embodiments, the fungus can include a genus selected from *Candida* spp, *Epidermophyton* spp, *Histoplasma* spp, *Trichophyton* spp, *Microsporum* spp, *Blastomyces* spp, *Histoplasma* spp, *Cryptococcus* spp, *Coccidioides* spp, *Pneumocystis* spp, *Saccharomyces* spp, *Aspergillus* spp, *Kluyveromyces* spp, *Schizosaccharomyces* spp, and *Streptomyces* spp. In some embodiments, the *Candida* spp can include *C. albicans, C. glabrata, C. rugosa, C. parapsilosis, C. tropicalis*, and *C. dubliniensis*. In some embodiments, the *Epidermophyton* spp is *E. flocco-* sum. In some embodiments, the sensitivity of the cell is increased at least about 2-fold compared to a cell not contacted with phenyl ethanol. In some embodiments, the sensitivity of the cell is increased at least about 5-fold compared to a cell not contacted with phenyl ethanol. In some embodiments, the sensitivity of the cell is increased at least about 20-fold compared to a cell not contacted with phenyl ethanol. In some embodiments, the cell is selected from the group consisting of *Candida* spp, *Epidermophyton* spp, *Histoplasma* spp, *Trichophyton* spp, *Microsporum* spp, *Blastomyces* spp, *Histoplasma* spp, *Cryptococcus* spp, *Coccidioides* spp *Pneumocystis* spp, *Saccharomyces* spp, *Aspergillus* spp, *Kluyveromyces* spp, *Schizosaccharomyces* spp, and *Streptomyces* spp. In some embodiments, the *Candida* spp is selected from the group consisting of *C. albicans, C. glabrata, C. rugosa, C. parapsilosis, C. tropicalis*, and *C. dubliniensis*. In some embodiments, the *Epidermophyton* spp is *E. floccosum*. In some embodiments, the antifungal agent is selected from the group consisting of a polyene, an imidazole, a triazole, a thiazole, an allylamine, Sordarin, Flucytosine and an echinocandin. In some embodiments, the polyene is selected from the group consisting of Amphotericin B, Candicidin, Filipin, Hamycin, Natamycin and Rimocidin. In some embodiments, the imidazole is selected from the group consisting of Bifonazole, Butoconazole, Clotrimazole, Econazole, Fenticonazole, Isoconazole, Ketoconazole, Luliconazole, Miconazole, Omoconazole, Oxiconazol, Sertaconazole, Sulconazole, and Tioconazole. In some embodiments, the triazole is selected from the group consisting of Albaconazole, Fluconazole, Isavuconazole, Itraconazole, Posaconazole, Ravuconazole, Terconazole, and Voriconazole. In some embodiments, the thiazole comprises Abafungin. In some embodiments, the allylamine is selected from the group consisting of Amorolfin, Butenafine, Naftifine, and Terbinafine. In some embodiments, the echinocandin is selected from the group consisting of Anidulafungin and Micafungin.

In some embodiments, a method of increasing the sensitivity of a fungal cell to an antifungal agent is provided wherein the method comprises contacting the cell with a compound of Formula I in combination with the antifungal agent

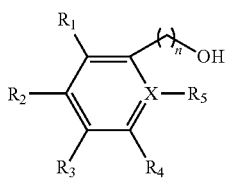

Formula I wherein X is selected from C, N, S and O;
$R_1$-$R_5$ is each independently selected from hydrogen, $C_1$ to $C_6$ alkyl, $C_1$ to $C_6$ substituted alkyl, $C_1$ to $C_6$ alkenyl, $C_1$ to $C_6$ substituted alkenyl; aryl, heteroaryl, alkoxy, and aryloxy; and n is 0, 1, 2, 3, 4, 5 or 6. In some embodiments, the sensitivity of the cell is increased at least about 2-fold compared to a cell not contacted with phenyl ethanol. In some embodiments, the sensitivity of the cell is increased at least about 5-fold compared to a cell not contacted with phenyl ethanol. In some embodiments, the sensitivity of the cell is increased at least about 20-fold compared to a cell not contacted with phenyl ethanol. In some embodiments, the cell is selected from the group consisting of *Candida* spp, *Epidermophyton* spp, *Histoplasma* spp, *Trichophyton* spp, *Microsporum* spp, *Blastomyces* spp, *Histoplasma* spp, *Cryptococcus* spp, *Coccidioides* spp *Pneumocystis* spp, *Saccharomyces* spp, *Aspergillus* spp, *Kluyveromyces* spp, *Schizosaccharomyces* spp, and *Streptomyces* spp. In some embodiments, the *Candida* spp is selected from the group consisting of *C. albicans, C. glabrata, C. rugosa, C. parapsilosis, C. tropicalis*, and *C. dubliniensis*. In some embodiments, the *Epidermophyton* spp is *E. floccosum*. In some embodiments, the antifungal agent is selected from the group consisting of a polyene, an imidazole, a triazole, a thiazole, an allylamine, Sordarin, Flucytosine and an echinocandin. In some embodiments, the polyene is selected from the group consisting of Amphotericin B, Candicidin, Filipin, Hamycin, Natamycin and Rimocidin. In some embodiments, the imidazole is selected from the group consisting of Bifonazole, Butoconazole, Clotrimazole, Econazole, Fenticonazole, Isoconazole, Ketoconazole, Luliconazole, Miconazole, Omoconazole, Oxiconazol, Sertaconazole, Sulconazole, and Tioconazole. In some embodiments, the triazole is selected from the group consisting of Albaconazole, Fluconazole, Isavuconazole, Itraconazole, Posaconazole, Ravuconazole, Terconazole, and Voriconazole. In some embodiments, the thiazole comprises Abafungin. In some embodiments, the allylamine is selected from the group consisting of Amorolfin, Butenafine, Nafti- In some embodiments, a method of treating and preventing a fungal infection is provided, wherein the method comprises administering an effective amount of phenyl ethanol in combination with an antifungal agent to a subject in need thereof. In some embodiments, the subject is mammalian. In some embodiments, the subject is human. In some embodiments, the subject is suffering from an autoimmune disorder. In some embodiments, the autoimmune disorder is a result of chemotherapy. In some embodiments, the autoimmune disorder is a result of an organ transplant. In some embodiments, the fungal infection is selected from the group consisting of *Candida* spp, *Epidermophyton* spp, *Histoplasma* spp, *Trichophyton* spp, *Microsporum* spp, *Blastomyces* spp, *Histoplasma* spp, *Cryptococcus* spp, *Coccidioides* spp *Pneumocystis* spp, *Saccharomyces* spp, *Aspergillus* spp, *Kluyveromyces* spp, *Schizosaccharomyces* spp, and *Streptomyces* spp. In some embodiments, the *Candida* spp is selected from the group consisting of *C. albicans, C. glabrata, C. rugosa, C. parapsilosis, C. tropicalis*, and *C. dubliniensis*. In some embodiments, the *Epidermophyton* spp is *E. floccosum*. In some embodiments, the antifungal agent is selected from the group consisting of a polyene, an imidazole, a triazole, a thiazole, an allylamine, and an echinocandin. In some embodiments, the polyene is selected from the group consisting of Amphotericin B, Candicidin, Filipin, Hamycin, Natamycin and Rimocidin. In some embodiments, the imidazole is selected from the group consisting of Bifonazole, Butoconazole, Clotrimazole, Econazole, Fenticonazole, Isoconazole, Ketoconazole, Luliconazole, Miconazole, Omoconazole, Oxiconazol, Sertaconazole, Sulconazole, and Tioconazole. In some embodiments, the triazole is selected from the group consisting of Albaconazole, Fluconazole, Isavuconazole, Itraconazole, Posaconazole, Ravuconazole, Terconazole, and Voriconazole. In some embodiments, the thiazole comprises Abafungin. In some embodiments, the allylamine is selected from the group consisting of Amorolfin, Butenafine, Naftifine, and Terbinafine. In some embodiments, the echinocandin is selected from the group consisting of Anidulafungin and Micafungin.

In some embodiments, a pharmaceutical composition is provided, wherein the pharmaceutical composition comprises phenyl ethanol, an antifungal agent and a pharmaceutical acceptable carrier. In some embodiments, the phenyl ethanol comprises a concentration of 625 uM to 10 mM. In some embodiments, the pharmaceutical composition is suitable for topical administration. In some embodiments, the composition is selected from the group consisting of an aerosol, powder, cream, paste, solution, suspension, and gel. In some embodiments, the pharmaceutical composition is suitable for intravenous administration. In some embodiments, the antifungal agent is selected from the group consisting of a polyene, an imidazole, a triazole, a thiazole, an allylamine, and an echinocandin. In some embodiments, the polyene is selected from the group consisting of Amphotericin B, Candicidin, Filipin, Hamycin, Natamycin and Rimocidin. In some embodiments, the imidazole is selected from the group consisting of Bifonazole, Butoconazole, Clotrimazole, Econazole, Fenticonazole, Isoconazole, Ketoconazole, Luliconazole, Miconazole, Omoconazole, Oxiconazol, Sertaconazole, Sulconazole, and Tioconazole. In some embodiments, the triazole is selected from the group consisting of Albaconazole, Fluconazole, Isavuconazole, Itraconazole, Posaconazole, Ravuconazole, Terconazole, and Voriconazole. In some embodiments, the thiazole comprises Abafungin. In some embodiments, the allylamine is selected from the group consisting of Amorolfin, Butenafine, Naftifine, and Terbinafine. In some embodiments, the echinocandin is selected from the group consisting of Anidulafungin and Micafungin. In some embodiments, the antifungal coating comprises phenyl ethanol. In some embodiments, the antifungal coating further comprises an antifungal agent. In some embodiments the composition comprises preservatives, stabilizers and/or dyes. In some embodiments, the preservatives are selected from a group consisting of sodium benzoate, ascorbic acid and esters of p-hydroxybenzoic acid. In some embodiments, the composition comprises antioxidants. In some embodiments, the composition comprises suspending agents. In some embodiments the composition comprises an excipient. In some embodiments the excipient is selected from a group consisting of water, saline, dextrose, mannitol, lactose, lecithin, albumin, sodium glutamate, cysteine hydrochloride, and the like. In some embodiments, the compositions are formulated as tablets, pills, capsules, liquids, gels, syrups, slurries or suspensions for oral ingestion by the patient in need. In some embodiments, the composition is formulated as a suspension. In some embodiments, the suspension is an oily suspension comprising lipophilic solvents or vehicles. In some embodiments, the lipophilic solvents or vehicles comprise fatty oils such as sesame oil, or other organic oils such as soybean, grapefruit or almond oils, or synthetic fatty acid esters, such as ethyl oleate or triglycerides, or liposomes. In some embodiments herein the composition for oral use is provided. In some embodiments, the composition for oral use comprises excipients, wherein the excipients are selected from a group consisting of sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). In some embodiments, the composition comprises concentrated sugar solutions, wherein the concentrated sugar solutions are selected from a group consisting of gum arabic, talc, polyvinyl pyrrolidone, carbopol gel, polyethylene glycol, and/or titanium dioxide, lacquer solutions, and suitable organic solvents and solvent mixtures. In some embodiments, the composition comprises active ingredients. In some embodiments, the active ingredients are selected from a group consisting of alcohols, esters, and sulfated aliphatic alcohols. In some embodiments, the composition further comprises excipients. In some embodiments, the excipients comprise sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like. In some embodiments, the composition comprises suspension agents and/or lubricants. In some embodiments, the suspension agents and/or lubricants comprise magnesium stearate, talc, hardened oil and the like may be used as smoothing agents; coconut oil, olive oil, sesame oil, peanut oil or soya. In some embodiments, the composition comprises suspension agents. In some embodiments, the suspension agent comprises cellulose acetate phthalate, derivatives of a carbohydrate such as cellulose or sugar, or methylacetate-methacrylate copolymer as a derivative of polyvinyl. In some embodiments, the composition comprises plasticizers. In some embodiments, the plasticizers comprise ester phthalates. In some embodiments, wherein the compositions are administered non-orally, the compositions are administered as an aqueous suspension, an oily preparation or the like or as a drip, suppository, salve or ointment. In some embodiments, wherein the composition is administered via injection, the composition is administered subcutaneously, intraperitoneally, intravenously or intramuscularly. In some embodiments, the compositions described herein are formulated into a single pill or tablet. In some embodiments, the pill or tablet has a mass from 10 mg to 2000 mg. In some embodiments, the pill or tablet has a mass from 100 mg to 1500 mg. In some embodiments, the pill or tablet has a mass from 500 mg to 1200 mg. In some embodiments, the pill or tablet has a mass from 800 mg to 1100 mg.

In some embodiments, a medical device comprising an antifungal coating is provided, wherein the antifungal coating comprises phenyl ethanol. In some embodiments, the antifungal coating further comprises an antifungal agent. In some embodiments, the medical device is selected from the group consisting of a catheter, an endoscope, a laryngoscope, a tube for feeding, a tube for drainage, a tube for endotracheal use, a guide wire, a condom, a glove, a wound dressing, a contact lens, an implant, an extracorporeal blood conduit, a membrane for dialysis, a blood filter, and a device for circulatory assistance. In some embodiments, the antifungal agent is selected from the group consisting of a polyene, an imidazole, a triazole, a thiazole, an allylamine, and an echinocandin. In some embodiments, the polyene is selected from the group consisting of Amphotericin B, Candicidin, Filipin, Hamycin, Natamycin and Rimocidin. In some embodiments, the imidazole is selected from the group consisting of Bifonazole, Butoconazole, Clotrimazole, Econazole, Fenticonazole, Isoconazole, Ketoconazole, Luliconazole, Miconazole, Omoconazole, Oxiconazol, Sertaconazole, Sulconazole, and Tioconazole. In some embodiments, the triazole is selected from the group consisting of Albaconazole, Fluconazole, Isavuconazole, Itraconazole, Posaconazole, Ravuconazole, Terconazole, and Voriconazole. In some embodiments, the thiazole comprises Abafungin. In some embodiments, the allylamine is selected from the group consisting of Amorolfin, Butenafine, Naftifine, and. Terbinafine. In some embodiments, the echinocandin is selected from the group consisting of Anidulafungin and Micafungin.

In some embodiments, a method of manufacturing a medical device is provided, wherein the method comprises coating the medical device with a coating comprising phenyl ethanol and an antifungal agent. In some embodiments, the medical device is selected from the group consisting of a catheter, an endoscope, a laryngoscope, a tube for feeding, a tube for drainage, a tube for endotracheal use, a guide wire, a condom, a glove, a wound dressing, a contact lens, am implant, an extracorporeal blood conduit, a membrane for dialysis, a blood filter, and a device for circulatory assistance. In some embodiments, the antifungal agent is selected from the group consisting of a polyene, an imidazole, a triazole, a thiazole, an allylamine, and an echinocandin. In some embodiments, the polyene is selected from the group consisting of Amphotericin B, Candicidin, Hamycin, Natamycin and Rimocidin. In some embodiments, the imidazole is selected from the group consisting of Bifonazole, Butoconazole, Clotrimazole, Econazole, Fenticonazole, Isoconazole, Ketoconazole, Luliconazole, Miconazole, Omoconazole, Oxiconazol, Sertaconazole, Sulconazole, and Tioconazole. In some embodiments, the triazole is selected from the group consisting of Albaconazole, Fluconazole, Isavuconazole, Itraconazole, Posaconazole, Ravuconazole, Terconazole, and Voriconazole. In some embodiments, the thiazole comprises Abafungin. In some embodiments, the allylamine is selected from the group consisting of Amorolfin, Butenafine, Naftifine, and Terbinafine. In some embodiments, the echinocandin is selected from the group consisting of Anidulafungin and Micafungin.

In some embodiments, a method of screening or testing a composition for fungal targets is provided, wherein the method comprises providing a concentration of phenyl ethanol, providing a concentration of an antifungal agent and culturing fungal cells under conditions wherein the fungal cells are in contact with the concentration of antifungal agent and the concentration of phenyl ethanol and wherein the fungal cells comprise modified alleles of a gene. In some embodiments, the gene contributes to the virulence and/or pathogenicity of the fungal cells to a host organism. In some embodiments, the fungal cells are selected from the group consisting of *Candida* spp, *Epidermophyton* spp, *Histoplasma* spp, *Trichophyton* spp, *Microsporum* spp, *Blastomyces* spp, *Histoplasma* spp, *Cryptococcus* spp, *Coccidioides* spp *Pneumocystis* spp, *Saccharomyces* spp, *Aspergillus* spp, *Kluyveromyces* spp, *Schizosaccharomyces* spp, and *Streptomyces* spp. In some embodiments, the *Candida* spp is selected from the group consisting of *C. albicans, C. glabrata, C. rugosa, C. parapsilosis, C. tropicalis*, and *C. dubliniensis*. In some embodiments, the *Epidermophyton* spp is *E. floccosum*. In some embodiments, the antifungal agent is selected from the group consisting of a polyene, an imidazole, a triazole, a thiazole, an allylamine, and an echinocandin. In some embodiments, the polyene is selected from the group consisting of Amphotericin B, Candicidin, Filipin, Hamycin, Natamycin and Rimocidin. In some embodiments, the imidazole is selected from the group consisting of Bifonazole, Butoconazole, Clotrimazole, Econazole, Fenticonazole, Isoconazole, Ketoconazole, Luliconazole, Miconazole, Omoconazole, Oxiconazol, Sertaconazole, Sulconazole, and Tioconazole. In some embodiments, the triazole is selected from the group consisting of Albaconazole, Fluconazole, Isavuconazole, Itraconazole, Posaconazole, Ravuconazole, Terconazole, and Voriconazole. In some embodiments, the thiazole comprises Abafungin. In some embodiments, the allylamine is selected from the group consisting of Amorolfin, Butenafine, Naftifine, and Terbinafine. In some embodiments, the echinocandin is selected from the group consisting of Anidulafungin and Micafungin.

In some embodiments, a method of increasing the sensitivity of a fungal cell to an antifungal agent is provided, wherein the method comprises contacting the cell with an enamine in combination with the antifungal agent. In some embodiments, the sensitivity of the cell is increased at least about 2-fold compared to a cell not contacted with the enamine. In some embodiments, the sensitivity of the cell is increased at least about 5-fold compared to a cell not contacted with the enamine. In some embodiments, the sensitivity of the cell is increased at least about 20-fold compared to a cell not contacted with the enamine. In some embodiments, the cell is selected from the group consisting of *Candida* spp, *Epidermophyton* spp, *Histoplasma* spp, *Trichophyton* spp, *Microsporum* spp, *Blastomyces* spp, *Histoplasma* spp, *Cryptococcus* spp, *Coccidioides* spp *Pneumocystis* spp, *Saccharomyces* spp, *Aspergillus* spp, *Kluyveromyces* spp, *Schizosaccharomyces* spp, and *Streptomyces* spp. In some embodiments, the *Candida* spp is selected from the group consisting of *C. albicans, C. glabrata, C. rugosa, C. parapsilosis, C. tropicalis*, and *C. dubliniensis*. In some embodiments, the *Epidermophyton* spp is *E. floccosum*. In some embodiments, the antifungal agent is selected from the group consisting of a polyene, an imidazole, a triazole, a thiazole, an allylamine, Sordarin, Flucytosine and an echinocandin. In some embodiments, the polyene is selected from the group consisting of Amphotericin B, Candicidin, Filipin, Hamycin, Natamycin and Rimocidin. In some embodiments, the imidazole is selected from the group consisting of Bifonazole, Luliconazole, Clotrimazole, Econazole, Fenticonazole, Isoconazole, Ketoconazole, Luliconazole, Miconazole, Omoconazole, Oxiconazol, Sertaconazole, Sulconazole, and Tioconazole. In some embodiments, the triazole is selected from the group consisting of Albaconazole, Fluconazole, Isavuconazole, Itraconazole, Posaconazole, Ravuconazole, Terconazole, and Voriconazole. In some embodiments, the thiazole comprises Abafungin. In some embodiments, the allylamine is selected from the group consisting of Amorolfin, Butenafine, Naftifine, and Terbinafine. In some embodiments, the echinocandin is selected from the group consisting of Anidulafungin and Micafungin.

In some embodiments, a method of treating and preventing a fungal infection is provided, wherein the method comprises administering an effective amount of an enamine in combination with an antifungal agent to a subject in need thereof. In some embodiments, the subject is mammalian. In some embodiments, the subject is human. In some embodiments, the subject is suffering from an autoimmune disorder. In some embodiments, the autoimmune disorder is a result of chemotherapy. In some embodiments, the autoimmune disorder is a result of an organ transplant. In some embodiments, the fungal infection is selected from the group consisting of *Candida* spp, *Epidermophyton* spp, *Histoplasma* spp, *Trichophyton* spp, *Microsporum* spp, *Blastomyces* spp, *Histoplasma* spp, *Cryptococcus* spp, *Coccidioides* spp *Pneumocystis* spp, *Saccharomyces* spp, *Aspergillus* spp, *Kluyveromyces* spp, *Schizosaccharomyces* spp, and *Streptomyces* spp. In some embodiments, the *Candida* spp is selected from the group consisting of *C. albicans, C. glabrata, C. rugosa, C. parapsilosis, C. tropicalis*, and *C. dubliniensis*. In some embodiments, the *Epi-*

*dermophyton* spp is *E. floccosum*. In some embodiments, the antifungal agent is selected from the group consisting of a polyene, an imidazole, a triazole, a thiazole, an allylamine, and an echinocandin. In some embodiments, the polyene is selected from the group consisting of Amphotericin B, Candicidin, Filipin, Hamycin, Natamycin and Rimocidin. In some embodiments, the imidazole is selected from the group consisting of Bifonazole, Butoconazole, Clotrimazole, Econazole, Fenticonazole, Isoconazole, Ketoconazole, Luliconazole, Miconazole, Omoconazole, Oxiconazol, Sertaconazole, Sulconazole, and Tioconazole. In some embodiments, the triazole is selected from the group consisting of Albaconazole, Fluconazole, Isavuconazole, Itraconazole, Posaconazole, Ravuconazole, Terconazole, and Voriconazole. In some embodiments, the thiazole comprises Abafungin. In some embodiments, the allylamine is selected from the group consisting of Amorolfin, Butenafine, Naftifine, and Terbinafine. In some embodiments, the echinocandin is selected from the group consisting of Anidulafungin and Micafungin.

In some embodiments, a pharmaceutical composition is provided, wherein the composition comprises an enamine, an antifungal agent and a pharmaceutical acceptable carrier. In some embodiments, the enamine comprises a concentration of 625 uM to 10 mM. In some embodiments, the pharmaceutical composition is suitable for topical administration. In some embodiments, the composition is selected from the group consisting of an aerosol, powder, cream, paste, solution, suspension, and gel. In some embodiments, the pharmaceutical composition is suitable for intravenous administration. In some embodiments, the antifungal agent is selected from the group consisting of a polyene, an imidazole, a triazole, a thiazole, an allylamine, and an echinocandin. In some embodiments, the polyene is selected from the group consisting of Amphotericin B, Candicidin, Filipin, Hamycin, Natamycin and Rimocidin. In some embodiments, the imidazole is selected from the group consisting of Bifonazole, Butoconazole, Clotrimazole, Econazole, Fenticonazole, Isoconazole, Ketoconazole, Luliconazole, Miconazole, Omoconazole, Oxiconazol, Sertaconazole, Sulconazole, and Tioconazole. In some embodiments, the triazole is selected from the group consisting of Albaconazole, Fluconazole, Isavuconazole, Itraconazole, Posaconazole, Ravuconazole, Terconazole, and Voriconazole. In some embodiments, the thiazole comprises Abafungin. In some embodiments, the allylamine is selected from the group consisting of Amorolfin, Butenafine, Naftifine, and Terbinafine. In some embodiments, the echinocandin is selected from the group consisting of Anidulafungin and Micafungin.

In some embodiments, a medical device comprising an antifungal coating is provided, wherein the antifungal coating comprises an enamine. In some embodiments, the antifungal coating further comprises an antifungal agent. In some embodiments, a method of manufacturing a medical device is provided, wherein the method comprises coating the medical device with a coating comprising an enamine and an antifungal agent. In some embodiments of the medical device or method, the medical device is selected from the group consisting of a catheter, an endoscope, a laryngoscope, a tube for feeding, a tube for drainage, a tube for endotracheal use, a guide wire, a condom, a glove, a wound dressing, a contact lens, an implant, an extracorporeal blood conduit, a membrane for dialysis, a blood filter, and a device for circulatory assistance. In some embodiments of the medical device or method, the antifungal agent is selected from the group consisting of a polyene, an imidazole, a triazole, a thiazole, art allylamine, and an echinocandin. In some embodiments of the medical device or method, the polyene is selected from the group consisting of Amphotericin B, Candicidin, Filipin, Hamycin, Natamycin and Rimocidin. In some embodiments of the medical device or method, the imidazole is selected from the group consisting of Bifonazole, Butoconazole, Clotrimazole, Econazole, Fenticonazole, Isoconazole, Ketoconazole, Luliconazole, Miconazole, Omoconazole, Oxiconazol, Sertaconazole, Sulconazole, and Tioconazole. In some embodiments of the medical device or method, the triazole is selected from the group consisting of Albaconazole, Fluconazole, Isavuconazole, Itraconazole, Posaconazole, Ravuconazole, Terconazole, and Voriconazole. In some embodiments of the medical device or method, the thiazole comprises Abafungin. In some embodiments of the medical device or method, the allylamine is selected from the group consisting of Amorolfin, Butenafine, Naftifine, and Terbinafine. In some embodiments of the medical device or method, the echinocandin is selected from the group consisting of Anidulafungin and Micafungin.

In some embodiments, a method of screening or testing a composition for fungal targets is provided, wherein the method comprises providing a concentration of an enamine, providing a concentration of an antifungal agent, and culturing fungal cells under conditions wherein the fungal cells are in contact with the concentration of antifungal agent and the concentration of an enamine and wherein the fungal cells comprise modified alleles of a gene. In some embodiments, the gene contributes to the virulence and/or pathogenicity of the fungal cells to a host organism. In some embodiments, the fungal cells are selected from the group consisting of *Candida* spp, *Epidermophyton* spp, *Histoplasma* spp, *Trichophyton* spp, *Microsporum* spp, *Blastomyces* spp, *Histoplasma* spp, *Cryptococcus* spp, *Coccidioides* spp *Pneumocystis* spp, *Saccharomyces* spp, *Aspergillus* spp, *Kluyveromyces* spp, *Schizosaccharomyces* spp, and *Streptomyces* spp. In some embodiments, the *Candida* spp is selected from the group consisting of *C. albicans, C. glabrata, C. rugosa, C. parapsilosis, C. tropicalis*, and *C. dubliniensis*. In some embodiments, the *Epidermophyton* spp is *E. floccosum*. In some embodiments, the antifungal agent is selected from the group consisting of a polyene, an imidazole, a triazole, a thiazole, an allylamine, and an echinocandin. In some embodiments, the polyene is selected from the group consisting of Amphotericin B, Candicidin, Filipin, Hamycin, Natamycin and Rimocidin. In some embodiments, the imidazole is selected from the group consisting of Bifonazole, Butoconazole, Clotrimazole, Econazole, Fenticonazole, Isoconazole, Ketoconazole, Luliconazole, Miconazole, Omoconazole, Oxiconazole, Sertaconazole, Sulconazole, and Tioconazole. In some embodiments, the triazole is selected from the group consisting of Albaconazole, Fluconazole, Isavuconazole, Itraconazole, Posaconazole, Ravuconazole, Terconazole, and Voriconazole. In some embodiments, he thiazole comprises Abafungin. In some embodiments, the allylamine is selected from the group consisting of Amorolfin, Butenafine, Naftifine, and Terbinafine. In some embodiments, the echinocandin is selected from the group consisting of Anidulafungin and Micafungin.

The term "comprising" as used herein is synonymous with "including," "containing," or "characterized by," and is inclusive or open-ended and does not exclude additional, unrecited elements or method steps.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A pharmaceutical composition comprising:
a compound having a structure of at least one of:

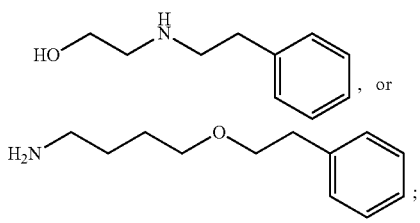

, or

;

an additional antifungal agent; and
a pharmaceutical acceptable carrier.

2. The pharmaceutical composition of claim 1, wherein the pharmaceutical composition is selected from the group consisting of an aerosol, powder, cream, paste, solution, suspension, and gel.

3. The pharmaceutical composition of claim 1, wherein the additional antifungal agent is selected from the group consisting of a polyene, an imidazole, a triazole, a thiazole, an allylamine, and an echinocandin.

4. The pharmaceutical composition of claim 1, wherein the additional antifungal agent is selected from the group consisting of Bifonazole, Butoconazole, Clotrimazole, Econazole, Fenticonazole, Isoconazole, Ketoconazole, Luliconazole, Miconazole, Omoconazole, Oxiconazol, Sertaconazole, Sulconazole, Tioconazole, Albaconazole, Fluconazole, Isavuconazole, Itraconazole, Posaconazole, Ravuconazole, Terconazole, Voriconazole, Abafungin, Amorolfin, Butenafine, Naftifine, Terbinafine, Anidulafungin, Sordarin, Flucytosine and Micafungin.

5. The pharmaceutical composition of claim 1, wherein the compound has the following structure:

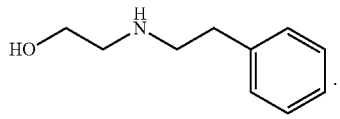 [SMILES: OCCNCCc1ccccc1]

6. The pharmaceutical composition of claim 1, wherein the compound has the following structure:

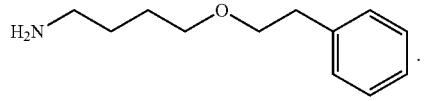

7. A method of increasing a sensitivity of a fungal cell to an antifungal agent, the method comprising:
contacting the fungal cell with a compound having a structure of at least one of:

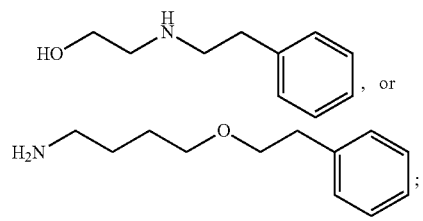

and an additional antifungal agent.

8. The method of claim 7, wherein the sensitivity of the fungal cell is increased at least about 2-fold, 5-fold or 20-fold as compared to a fungal cell not contacted with the compound.

9. The method of claim 7, wherein the fungal cell is selected from the group consisting of *Candida* spp, *Epidermophyton* spp, *Histoplasma* spp, *Trichophyton* spp, *Microsporum* spp, *Blastomyces* spp, *Cryptococcus* spp, *Coccidioides* spp *Pneumocystis* spp, *Saccharomyces* spp, *Aspergillus* spp, *Kluyveromyces* spp, *Schizosaccharomyces* spp, and *Streptomyces* spp.

10. The method of claim 7, wherein the additional antifungal agent is selected from the group consisting of a polyene, an imidazole, a triazole, a thiazole, an allylamine, and an echinocandin.

11. The method of claim 7, wherein the additional antifungal agent is selected from the group consisting of Amphotericin B, Candicidin, Filipin, Hamycin, Natamycin, Rimocidin, Bifonazole, Butoconazole, Clotrimazole, Econazole, Fenticonazole, Isoconazole, Ketoconazole, Luliconazole, Miconazole, Omoconazole, Oxiconazol, Sertaconazole, Sulconazole, Tioconazole, Albaconazole, Fluconazole, Isavuconazole, Itraconazole, Posaconazole, Ravuconazole, Terconazole, Voriconazole, Abafungin, Amorolfin, Butenafine, Naftifine, Terbinafine, Anidulafungin, Sordarin, Flucytosine and Micafungin.

12. The method of claim 7, wherein the fungal cell is drug resistant.

13. The method of claim 7, wherein the compound has the following structure:

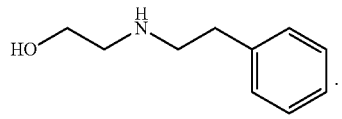

14. The method of claim 7, wherein the compound has the following structure:

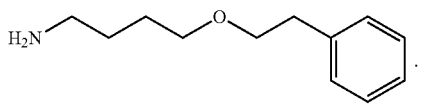 [SMILES: NCCCCOCCc1ccccc1]

15. A method of treating a fungal infection, the method comprising:
administering to a subject in need thereof an effective amount of a compound having a structure of at least one of:

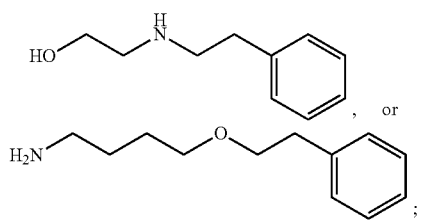

and an additional antifungal agent.

16. The method of claim 15, wherein the fungal infection is caused by a fungal cell selected from the group consisting of *Candida* spp, *Epidermophyton* spp, *Histoplasma* spp, *Trichophyton* spp, *Microsporum* spp, *Blastomyces* spp, *Cryptococcus* spp, *Coccidioides* spp *Pneumocystis* spp, *Saccharomyces* spp, *Aspergillus* spp, *Kluyveromyces* spp, *Schizosaccharomyces* spp, and *Streptomyces* spp.

17. The method of claim 15, wherein the additional antifungal agent is selected from the group consisting of a polyene, an imidazole, a triazole, a thiazole, an allylamine, and an echinocandin.

18. The method of claim 15, wherein the additional antifungal agent is selected from the group consisting of Amphotericin B, Candicidin, Filipin, Hamycin, Natamycin Rimocidin, Bifonazole, Butoconazole, Clotrimazole, Econazole, Fenticonazole, Isoconazole, Ketoconazole, Luliconazole, Miconazole, Omoconazole, Oxiconazol, Sertaconazole, Sulconazole, Tioconazole,Albaconazole, Fluconazole, Isavuconazole, Itraconazole, Posaconazole, Ravuconazole, Terconazole, Voriconazole, Abafungin, Amorolfin, Butenafine, Naftifine, Terbinafine, Anidulafungin, Sordarin, Flucytosine and Micafungin.

19. The method of claim 15, wherein the subject is immunocompromised.

20. The method of claim 15, wherein the fungal infection is drug resistant.

21. The method of claim 15, wherein the compound has the following structure:

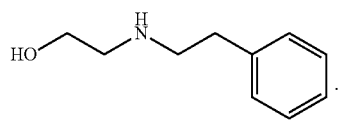

22. The method of claim 15, wherein the compound has the following structure:

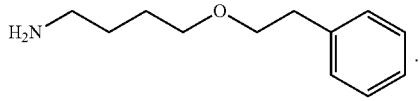

* * * * *